(12) United States Patent
Smith et al.

(10) Patent No.: US 10,918,679 B2
(45) Date of Patent: *Feb. 16, 2021

(54) COMPOSITIONS AND METHODS FOR REDUCING BLOOD ALCOHOL CONTENT

(71) Applicant: LIFE WELL LIVED, LLC, Austin, TX (US)

(72) Inventors: Roxanne Smith, Austin, TX (US); Jonathan Rinker, Austin, TX (US); Kent Howard, Austin, TX (US)

(73) Assignee: LIFE WELL LIVED, LLC, Austin, TX (US)

(*) Notice: Subject to any disclaimer, the term of this patent is extended or adjusted under 35 U.S.C. 154(b) by 147 days.

This patent is subject to a terminal disclaimer.

(21) Appl. No.: 15/445,299

(22) Filed: Feb. 28, 2017

(65) Prior Publication Data

US 2017/0326185 A1 Nov. 16, 2017

Related U.S. Application Data

(63) Continuation of application No. 14/850,165, filed on Sep. 10, 2015, now abandoned, which is a continuation of application No. 13/796,692, filed on Mar. 12, 2013, now Pat. No. 9,161,957.

(60) Provisional application No. 61/679,308, filed on Aug. 3, 2012, provisional application No. 61/691,900, filed on Aug. 22, 2012.

(51) Int. Cl.

| | |
|---|---|
| A61K 35/744 | (2015.01) |
| A61K 31/7084 | (2006.01) |
| A61K 35/745 | (2015.01) |
| A61K 35/747 | (2015.01) |
| A61K 35/74 | (2015.01) |
| A61K 33/30 | (2006.01) |
| A61K 31/122 | (2006.01) |
| A61K 31/455 | (2006.01) |
| A61K 31/355 | (2006.01) |
| A61K 31/4415 | (2006.01) |
| A61K 31/714 | (2006.01) |
| A61K 9/00 | (2006.01) |
| A61K 45/06 | (2006.01) |
| A61K 35/00 | (2006.01) |

(52) U.S. Cl.
CPC .......... *A61K 35/747* (2013.01); *A61K 9/0053* (2013.01); *A61K 31/122* (2013.01); *A61K 31/355* (2013.01); *A61K 31/4415* (2013.01); *A61K 31/455* (2013.01); *A61K 31/7084* (2013.01); *A61K 31/714* (2013.01); *A61K 33/30* (2013.01); *A61K 35/745* (2013.01); *A61K 45/06* (2013.01); *A61K 2035/11* (2013.01)

(58) Field of Classification Search
None
See application file for complete search history.

(56) References Cited

U.S. PATENT DOCUMENTS

| | | |
|---|---|---|
| 5,759,539 A | 6/1998 | Whitmire |
| 7,544,356 B2 | 6/2009 | Lim et al. .............. 424/93.45 |
| 7,842,495 B2 | 11/2010 | Yamahira et al. ......... 435/252.9 |
| 7,858,336 B1 | 12/2010 | Garner et al. .................. 435/41 |
| 8,440,242 B1 | 5/2013 | Grady |
| 2004/0126870 A1 | 7/2004 | Arigoni et al. ............ 435/252.2 |
| 2005/0271739 A1 | 12/2005 | Wang .......................... 424/562 |
| 2006/0233774 A1 | 10/2006 | Lim et al. .................. 424/93.45 |
| 2006/0246561 A1 | 11/2006 | Hummel et al. .............. 435/155 |
| 2006/0263385 A1 | 11/2006 | Gare ........................ 424/195.16 |
| 2006/0269535 A1 | 11/2006 | Naidu et al. ................. 424/94.1 |
| 2009/0054351 A1 | 2/2009 | Matuschka-Greiffenclau |
| 2010/0047320 A1 | 2/2010 | Prakash et al. ............... 424/439 |
| 2010/0183559 A1 | 7/2010 | Van Sinderen et al. ..... 424/93.2 |

FOREIGN PATENT DOCUMENTS

| | | | |
|---|---|---|---|
| CN | 1377586 | 11/2002 | |
| CN | 1705476 | 12/2005 | |
| CN | 1706479 | 12/2005 | |
| CN | 1853508 | 11/2006 | |
| EP | 2420147 A1 * | 2/2012 | ............ A61K 31/70 |
| JP | H07-53366 | 2/1995 | |
| JP | 2002530100 | 9/2002 | |
| JP | 2006298917 | 11/2006 | |
| JP | 2009153529 | 7/2009 | |
| JP | 2010-270101 | 12/2010 | |
| KR | 10-0142615 | 4/1998 | |
| KR | 10-0543115 | 1/2006 | |
| KR | 10-0609779 | 7/2006 | |

(Continued)

OTHER PUBLICATIONS

JL Quiles et al., "Coenzyme Q Concentration and Total Antioxidant Capacity of Human Milk at Different States of Lactation in Mother of Preterm and Full-term Infants," *Free Radical Research*, 2006: 40(2): 199-206.

(Continued)

*Primary Examiner* — Robert J Yamasaki
*Assistant Examiner* — Charles Zoltan Constantine
(74) *Attorney, Agent, or Firm* — Norton Rose Fulbright US LLP

(57) ABSTRACT

Disclosed are compositions and methods for reducing blood alcohol content following alcohol consumption. The inventive compositions and methods rapidly reduce blood alcohol content and alleviate symptoms of intoxication in a subject having an elevated blood alcohol content due to alcohol consumption.

8 Claims, 14 Drawing Sheets

(56) References Cited

FOREIGN PATENT DOCUMENTS

| WO | WO/87/001285 | 3/1987 |
|---|---|---|
| WO | WO/10/012074 | 2/2010 |

OTHER PUBLICATIONS

Lixia Xiao et al., "Study on the Protective Effects of Lactic Acid Bacteria on Acute Alcohol-Induced Liver in Jury in Mice," *Journal of Yangzhou University (Agricultural and Life Science Edition*, 2008; 29(4): 37-41 (English Abstract Provided).

Office Action issued in corresponding Chinese Application No. 201380041126.7, dated May 3, 2018.

Tetsu Johke et al., "Acid-Soluble Nucleotides of Colostrum, Milk, and Mammary Gland," *The Journal of Biochemistry*, 1963; 54(5): 388-397.

"Alcohol Metabolism", NIAAA, accessed Aug. 4, 2012, via http://alcoholism.about.com/cs/alerts/1/blnaa35.htm.

"Indigenous Bacteria in the Treatment of Asian Flush" (Abstract).

"The NADH Connection", CERI: Living with Alcohol, accessed Aug. 4, 2012, via http://www.ceri.com/alcohol.htm.

Agarwal and Goedde, "Pharmacogenetics of alcohol metabolism and alcoholism", *Pharmacogenetics*, 2(2):48-62, 1992. (Abstract).

Ammon et al., "First Pass Metabolism of Ethanol: Gastric or Hepatic, Mountain or Molehill", Hepatology Elsewhere, 25(5):1292-1294, 1997.

Baraona et al., "Gender differences in pharmacokinetics of alcohol", *Alcohol Clin. Exp. Res.*, 25(4):502-507, 2001. (Abstract).

Birley et al., "ADH single nucleotide polymorphism associations with alcohol metabolism in vivo", Hum. Mol. Genet., 18(8):1533-1542m 2009.

Bogen, "The Diagnosis of Drunkenness—a Quantitative Study of Acute Alcoholic Intoxication", California and Western Medicine, 26(6):778-783, 1927.

Bosron and Li, "Genetic polymorphism of human liver alcohol and aldehyde dehydrogenases, and their relationship to alcohol metabolism and alcoholism", American Association for the Study of Liver Diseases, 2005. (Abstract)

Caballeria et al., "Zinc administration improves gastric alcohol dehydrogenase activity and first pass metabolism of ethanol in alcohol-fed rats", Liver Unit, 21(9):1619-1622, 1997. (Abstract).

Cederbaum et al., "Role of oxidative stress in alcohol-induced liver injury", *Arch Toxicol.*, 83(6):519-548, 2009. (Abstract).

Chandramoulia et al., "An improved method of microencapsulation and its evaluation to protect *Lactobacillus* spp. in simulated gastric conditions", Journal of Microbiological Methods, 56(1):27-35, 2004. (Abstract).

Chiang et al., "Expression pattern, ethanol-metabolizing activities, and cellular localization of alcohol and aldehyde dehydrogenases in human large bowel: association of the functional polymorphisms of ADH and ALDH genes with hemorrhoids and colorectal cancer", *Alcohol*, 46(1)37-49, 2011. (Abstract).

Citizendia, "Short-term effects of alcohol", Citizendia.org, accessed Jul. 1, 2012, http://citizendia.org/Short-term_effets_of_alcohol.

Corcoran et al., "Survival of Probiotic Lactobacilli in Acidic Environments is Enhanced in the Presence of Metabolizable Sugars", *Applied and Environmental Microbiology*, 71(6):3060-3067, 2005.

Crabb and Liangpunsakul, "Acetaldehyde generating enzymes systems: roles of alcohol dehydrogenase, CYP2E1 and catalase, and speculations on the role of other enzymes and processes", Novartis Found Symp., 285:4-16, 2007. (Abstract).

Crabb et al., "Overview of the role of alcohol dehydrogenase and aldehyde dehydrogenase and their variants in the genesis of alcohol-related pathology", Proceeding of the Nutrition Society, 63:49-63, 2004.

Dohmen et al., "Ethnic differences in gastric sigma-alcohol dehydroagenase activity and ethanol first-pass metabolism", *Alcohol Clin. Exp. Res.*, 20(9):1569-1576, 1996. (Abstract).

Dunne et al., "In vitro selection criteria for probiotic bacteria of human origin: correlation with in vivo findings", *The American Journal of Clinical Nutrition*, 73(suppl):386S-392S, 2001.

Edenberg, "The genetics of alcohol metabolism role of alcohol dehydrogenase and aldehyde dehydrogenase variants", Alcohol Res. Health, 30(1):5-13, 2007. (Abstract).

Extended European Search Report in European Application No. 13824903.2 dated Oct. 27, 2015.

Farnworth, "The Evidence to Support Health Claims for Probiotics", The Journal of Nutrition, 138:1250S-1254S, 2008.

Farres et al., "Alcohol dehydrogenase of class IV (aa-ADH) from human stomach cDNA sequence and structure/function relationships", Eur. J. Biochem., 224:549-557, 1994.

Forsyth, et al., "Lactobacillus GG treatment ameliorates alcohol-induced intestinal oxidative stress, gut leakiness, and liver injury in a rat model of alcoholic steatohepatitis" Alcohol. 43(2):163-172, 2009.

Frei, "Reactive Oxygen Species and Antioxidant Vitamins", The Liuns Pauling Institute, 1997, 3 pages, accessed Aug. 22, 2012, via http://lpi.oregonstate.edu/f-w97/reactive.html.

Frezza et al., "High blood alcohol levels in women. The role of decreased gastric alcohol dehydrogenase activity and first-pass metabolism", N. Engl. J. Med., 322(2):95-99, 1990.

Fuller, "Probiotics in human medicine", Gut, 32:439-442, 1991.

Gergel and Cederbaum, Inhibition of the catalytic activity of alcohol dehydrogenase by nitric oxide is associated with S nitrosylation and the release of zinc, Biochemistry, 35(50):16186-16194, 1996. (Abstract).

Goldin et al., "Survival of *Lactobacillus* species (strain GG) in human gastrointestinal tract", Digestive Diseases and Sciences, 37(1):121-128, 1992. (Abstract).

Grant et al., "Blood alcohol concentration and psychomotor effects", British Journal of Anesthesia, 85(3):401-406, 2000.

Guerin et al., "Protection of Bifidobacteria Encapsulated in Polysaccharide-Protein Gel Beads against Gastric Juice and Bile", Journal of Food Protection, 66(11):2076-2084, 2003. (Abstract).

Gugler, "H2-antagonists and alcohol. Do they interact?", *Drug. Saf.*, 10(4):271-280, 1994. (Abstract).

Haber et al., "Metabolism of Alcohol by Human Gastric Cells: Relation to First-Pass Metabolism", Gastroenterology, 111:863-870, 1996.

Hamilton-Miller et al., "Public health issues arising from microbiological and labeling quality of foods and supplements containing probiotic microorganisms", Public Health Nutrition, 2(2):223-229, 1999.

Harding, "Report on the Subcommittee on Alcohol: Technology, Pharmacology, and Toxicology", Center for Studies of Law in Action, 1999, 12 pages.

Hernandez-Tobias et al., "Natural alcohol exposure : is ethanol the main substrate for alcohol dehydrogenases in animals?", Chem. Biol. Interact., 191(1-3):14-25, 2011. (Abstract).

Hipolito et al., "Brain metabolism of ethanol and alcoholism: an update", *Curr. Drug. Metab.*, 8(7):716-27, 2007. (Abstract).

International Search Report and Written Opinion issued in PCT Application No. PCT/US2013/052500, dated Oct. 31, 2013.

Jacobsen et al., "Screening of Probiotic Activities of Forty-Seven Strains of *Lactobacillus* spp. by in Vitro Techniques and Evaluation of the Colonization Ability of Five Selected Strains in Humans", Applied and Environmental Microbiology, 65(11):4949-4956, 1999.

Jamieson Laboratories, "Lactobacillus Acidophilus Probiotic Complex", Jamieson™ Laboratoires, Jan. 19, 2005.

Jelski and Szmitkowski, "Alcohol dehydrogenase ADH and aldehyde dehydrogenase ALDH in the cancer diseases", *Clin. Chim. Acta.*, 395(1-2):1-5, 2008. (Abstract).

Jelski et al., "Effects of H2-blockers on alcohol dehydrogenase (ADH) activity", *Pol. Merkur Lekarski*, 25(150):531-533, 2008. (Abstract).

Jokelainen et al. "In vitro acetaldehyde formation by human colonic bacteria", Gut, 35:1271-1274, 1994.

Jokelainen et al., "High intracolonic acetaldehyde values produced by a bacteriocolonic pathway for ethanol oxidation in piglets", Gut, 39:100-104, 1996.

Jokelainen et al., "In Vitro Alcohol Dehydrogenase Mediated Acetaldehyde Production by Aerobic Bacteria Representing the normal

(56) References Cited

OTHER PUBLICATIONS

Colonic Flora in Man", Alcoholism: Clinical and Experimental Research, 20(6):967-972, 1996. (Abstract).
Jones, "Pharmacokinetics of ethanol—Issues of forensic importance", *Forensic Sci Rev*, 23:91, 2011.
Julkunen et al., "First pass metabolism of ethanol—a gastrointestinal barrier against the systematic toxicity of ethanol", *Life Sci.*, 37(6):567-573, 1985. (Abstract).
Julkunen et al., "First pass metabolism of ethanol: An important determinant of blood levels after alcohol consumption", *Alcohol*, 2(3):437-441, 1985 (Abstract).
Kagi and Bailee, "The role of Zinc in Alcohol Dehydrogenase v. the Effect of Metal-Binding Agents on the Structure of the yeast Alcohol Dehydrogenase Molecule", the Journal of Biological Chemistry, 235(11):3188-3192, 1960.
Kirjavainen et al., "The ability of probiotic bacteria to bind to human intestinal mucus", *FEMS Microbiol. Lett.*, 167(2):185-189, 1998. (Abstract).
Klijn et al., "Lessons from the genomes of bifidobacteria", FEMS Microbiology Reviews, 29:491-509, 2005.
Koop, "Alcohol Metabolism's Damaging Effects on the Cell: A Focus on Reactive Oxygen Generation by the Enzyme Cytochrome P450 2E1", Alcohol Research & Health, 29(4):274-280, 2006.
Kunitoh et al., "Acetaldehyde as Well as Ethanol is Metabolized by Human CYP2E1", the Journal of Pharmacology and Experimental Therapeutics, 280(2):527-532, 1997.
Lambert et al., "Prevention of Alterations in Intestinal Permeability is Involved in Zinc Inhibition of Acute Ethanol-Induced Liver Damage in Mice", The Journal of Pharmacology and Experimental Therapeutics, 305(3):880-886, 2008.
Lane et al., "Alcohol effects on human risk taking", Psychopharmacology, 172:68-77, 2004.
Levitt et al., "Use of measurements of ethanol absorption from stomach and intestine to assess human ethanol metabolism", Am. J. Physiol Gastrointest. Liver Physiol, 273 :G951-G957, 1997.
Lieber et al., "First pass metabolism of ethanol", *Alcohol Alcohol Suppl.*, 2:163-169, 1994. (Abstract).
Lieber, "Ethanol metabolism, cirrhosis and alcoholism", *Clinica Chimica Acta*, 257:59-84, 1997.
Lim et al., "First pass metabolism of ethanol is predominantly gastric", *Alcohol Clin. Exp. Res.*, 17(6):1337-1344, 1993. (Abstract).
Liu et al., "Biomimetic enzyme nanocomplexes and their use as antidotes and preventive measures for alcohol intoxication", Nature Nanotechnology, Feb. 17, 2013, accessed Feb. 18, 2013, http://www.nature.com/nnano/journal/vaop/ncurrent/full/nnano.2012.264.html.
Mantle and Preedy, "Free radicals as mediators of alcohol toxicity", *Adverse Drug Reactions and Toxicological Reviews*, 18(4):235-252, 1999. (Abstract).
Mantle and Preedy, "Protective effects of cysteine, methionine and vitamin C on the stomach in chronically alcohol treated rats", Adverse Drug Reactions and Toxicological Reviews, 18(4):235-252, 1999. (Abstract).
Marteau et al., "Survival of Lactic Acid Bacteria in a Dynamic Model of the Stomach and Small Intestine: Validation and the Effects of Bile", *J. Dairy Sci.*, 80(6):1031-1037, 1997. (Abstract).
Meurman and Uittamol, "Oral microorganisms in the etiology of cancer", *Acta Odontol Scand.*, 66(6):321-326, 2008. (Abstract).
Mira et al., "Evidence for Free Radical Generation Due to NADH Oxidation by Aldehyde Oxidase During Ethanol Metabolism", *Arch Biochem Biophys.*, 318(1):53-58, 1995. (Abstract).
Moreno and Pares, "Purification and Characterization of a New Alcohol Dehydrogenase from Human Stomach", The Journal of Biological Chemistry, 266(2):1128-1133, 1991.
Nosova et al., "Acetaldehyde Production and Metabolism by Human Indigenous and Probiotic Lactobacillus and Bifidobacterium Strains", Alcohol & Alcoholism, 35(6):561-568, 2000.
Nosova et al., "Aldehyde Dehydrogenase Activity and Acetate Production by Aerobic Bacteria Representing the Normal Flora of Human Large Intestine", Alcohol & Alcoholism, 31(6):555-564, 1996.
Nosova et al., "Characteristics of Alcohol Dehydrogenases of Certain Aerobic Bacteria Representing Human Colonic Flora", Alcoholism: Clinical and Experimental Research, 21(3):489-494, 1997. (Abstract).
Nosova et al., "Characteristics of Aldehyde Dehydrogenase of Certain Aerobic Bacteria Representing Human Colonic Flora", Alcohol & Alcoholism, 33(3):273-280, 1998.
Nosova et al., "Ciprofloxacin Administration Decreases Enhanced Ethanol Elimination in Ethanol-Fed Rats", Alcohol & Alcoholism, 34(1):48-54, 1999.
Office Action issued in Japanese Application No. 2015-525482, dated May 10, 2017. (English Translation).
Oneta et al., "First pass metabolism of ethanol is strikingly influenced by the speed of gastric emptying", Gut, 43(5):612-619, 1998.
Orcutt, "Nanocapsules Sober Up Drunken Mice: Wrapping alcohol-digesting enzymes in a nanoscale polymer allows them to quickly reduce blood alcohol content", MIT Technology Review, Feb. 17, 2013, accessed Feb. 18, 2013, http://www.technologyreview.com/news/511261/nanocapsules-sober-up-drunken-mice/.
Orywal et al., "Alcohol dehydrogenase and aldehyde dehydrogenase in malignant diseases—Part II", *Pol. Merkur. Lekarski*, 25(146) : 184-187, 2008. (Abstract).
Ouwehand et al., "Probiotics: an overview of beneficial effects", *Anoinie van Leeuwenhock*, 82:279-289, 2002. (Abstract).
Parlesak et al., "First-pass metabolism of ethanol in human beings: effect of intravenous infusion of fructose", *Alcohol*, 34(2-3):121-125, 2004. (Abstract).
Pastino and Conolly, "Application of a Physiologically Based Pharmacokinetic model to Estimate the Bioavailability of Ethanol in Male Rats: Distinction between Gastric and Hepatic Pathways of Metabolic Clearance", *Toxicological Science*, 55:256-265, 2000.
Poschl and Seitz, "Alcohol and Cancer", Alcohol & Alcoholism, 39(3):155-165, 2004.
Purohit et al., "Alcohol, Intestinal Bacterial Growth, Intestinal Permeability to Endotoxin, and Medical Consequences: Summary of a Symposium", Alcohol, 42(5):349-361, 2008.
Racker, "Aldehyde Dehydrogenase, a Diphosphopyridine Nucleotide-Linked Enzyme", Department of Microbiology, pp. 883-892, 1948.
Ramchandani et al., "Research advances in ethanol metabolism", Pathol. Biol, 49(9):676-682, 2001. (Abstract).
Raskin and Sokoloff, "Enzymes Catalysing Ethanol Metabolism in Neural and Somatic Tissues of the Rat", *J. Neurochem*, 19(2):273-282, 1972. (Abstract).
Roine et al., "Effect of Concentration of Ingested Ethanol on Blood Alcohol Levels", *Alcohol Clin. Exp. Res.*, 15(4):734-738, 2006. (Abstract).
Salaspuro et al., "Ethanol oxidation and acetaldehyde production in vitro by human intestinal strains of *Escherichia coli* under aerobic, microaerobic, and anaerobic conditions", *Scand. J. Gastroenterol.*, 34(10):967-973, 1999. (Abstract).
Salaspuro, "Acetaldehyde, Microbes, and Cancer of the Digestive Tract", 40(2):183-208, 2003. (Abstract).
Salaspuro, "Bacteriocolonic pathway for ethanol oxidation: characteristics and implications", *Ann. Med.*, 28(3):195-200, 1996. (Abstract).
Salaspuro, "Microbial metabolism of ethanol and acetaldehyde and clinical consequences", Addiction Biology, 2(1):35-46, 1997. (Abstract).
Sanchez et al., "Low pH Adaptation and the Acid Tolerance Response of Bifidobacterium longum Biotype longum", *Appl. Environ. Microbiol.*, 73(20):6450-6459, 2007.
Satre et al., "The Complete Structure of Human Class IV Alcohol Dehydrogenase (Retinol Dehydrogenase) Determined from the ADH7 Gene", The Journal of Biological Chemistry, 269(22):15606-15612, 1994.
Saxelin et al., "Persistence of probiotic strains in the gastrointestinal tract when administered as capsules, yoghurt, or chees", International Journal of Food Microbiology, 8 pages, 2010.

(56) References Cited

OTHER PUBLICATIONS

Schell et al., "The genome sequences of Bifidobacterium longum reflects its adaptation to the human gastrointestinal tract", PNAS, 99(22):14422-14427, 2002.
Scott and Taylor, "Health-Related Effects of Genetic Variations of Alcohol-Metabolizing Enzymes in African Americans", Alcohol Research & Health, 30(1):18-21, 2007.
Segawa, et al., "Oral Administration of heat-killed Lactobacillus brevis SBC8803 ameliorates alcoholic liver disease in ethanol-containing diet-fed C57BL/6N mice." Int J Food Microbiol. 128(2):371-377, 2008.
Seitz and Becker, "Alcohol Metabolism and Cancer Risk", Alcohol Research & Health, 30(1):38-47, 2007.
Seitz and Meier, "The role of acetaldehyde in upper digestive tract cancer in alcoholics", Translational Research, 149(6):293-297, 2007.
Seitz and Oneta, "Gastrointestinal alcohol dehydrogenase", *Nutr Rev.*, 56(2):52-60, 1998. (Abstract).
Seitz and Poschl, "The Role of Gastrointestinal Factors in Alcohol Metabolism", Alcohol & Alcoholism, 32(5):543-549, 1997.
Seitz et al., "Alcohol and Cancer", Alcoholism: Clinical and Experimental Research, 25(5):1375-1435, 2001.
Seitz et al., "Ethanol metabolism in the gastrointestinal tract and its possible consequences", Alcohol Alcohol Suppl., 2:157-162, 1994. (Abstract).
Seitz et al., "Human gastric alcohol dehydrogenase activity: effect of age, sex, and alcoholism", Gut, 34:1433-1437, 1993.
Suddendorf, "Research on Alcohol Metabolism Among Asians and Its Implications for Understanding Causes of Alcoholism", Public Health Reports, 104(6):615-620, 1989.
Tillonen et al., "Role of Catalase in in Vitro Acetaldehyde formation by Human Colonic Contents", 2006. (Abstract).
Tillonena et al., "Ciprofloxacin decreases the rate of ethanol elimination in humans" (Abstract).
Turner et al., "A longitudinal study of ethanol and acetaldehyde in the exhaled breath of healthy volunteers using selected-ion flow-tube mass spectrometry", Rapid Communications in Mass Spectrometry, 20:61-68, 2006.
Vakevainen et al., "Acetaldehyde Production and Other ADH Related Characteristics of Aerobic Bacteria Isolated From Hypochlorhydric Human Stomach", Alcoholism: clinical and Experimental Research, 25(3):421-426, 2001. (Abstract).
Von Ossowski et al., "Mucosal Adhesion Properties of the Probiotic Lactobacillus rhamnosus GG SpaCBA and SpaFED Pilin Subunits", Applied and Environmental Microbiology, 76(7):2049-2057, 2010.
Walter, "Ecological Role of Lactobacilli in the Gastrointestinal Tract: Implications for Fundamental and Biomedical Research", Applied and Environmental Microbiology, 74(16):4985-4996, 2008.
Wang et al., "Effects of ingesting Lactobacillus- and Bifidobacterium-containing yogurt in subjects with colonized Helicobacter pylori", the American Journal of Clinical Nutrition, 80:737-741, 2004.
Wiese et al., "The Alcohol Hangover", Annals of Internal Medicine, 132(11):897-902, 2000.
World Health Organization, *Global status report on alcohol and health*, 2011.
Yang et al., "Silencing of cytosolic NADP+-dependent isocitrate dehydrogenase gene enhances ethanol-induced toxicity in HepG2 cells", *Arch Pharm Res.*, 33(7):1065-1071, 2010. (Abstract).
Yin et al., "Human stomach alcohol and aldehyde dehydrogenases: Comparison of expression pattern and activities in alimentary tract", Gastroenterology, 112(3):766-775, 1997. (Abstract).
Yin, "Alcohol dehydrogenase enzymology and metabolism", Alcohol Alcohol Suppl., 2:113-119, 1994. (Abstract).
Ylikahri et al., "Effects of Fructose and Glucose on Ethonol-Induced Metabolic Changes on the Intensity of Alcohol Intoxication and Hangover", European Journal of Clinical Investigation, 6(1):93-102, 2008. (Abstract).
Zakhari, "Overview: How is Alcohol Metabolized by the Body?", Alcohol Research & Health, 29(4):245-252, 2006.
Zhong et al., "The role of zinc deficiency in alcohol-induced intestinal barrier dysfunction", Am. J. Physiol. Gastrointest. Liver Physiol., 298:G625-G633, 2010.
Zhou et al., "Zinc supplementation prevents alcoholic liver injury in mice through attenuation of oxidative stress", Am. J. Pathol., 166(6):1681-1690, 2005.
Coarse et al., Use of Fructose in the Treatment of Acute Alcoholic Intoxication, *American Journal of Hospital Pharmacy*, 32(5):518-519, (1975).
Kim et al., "Effect of *Lactobacillus fermentum* MG590 on Alcohol Metabolism and Liver Function in Rats," *J. Microbiol. Biotechnol.*, 13(6):919-925, (2003).
Lee et al., Effects of *Panax Ginseng* on Blood Alcohol Clearance in Man, Clinical *and Experimental Pharmacology & Physiology*, 14:543-546, (1987).
Office Action issued in Japanese Application No. 2015-525482, dated Jan. 18, 2018.
Office Action Issued in Corresponding Canadian Patent Application No. 2,880,841, dated Jun. 19, 2019.
Office Action Issued in Corresponding European Patent Application No. 13824903.2, dated Aug. 1, 2019.
Vonghia, et al., "Acute Alcohol Intoxication," *European Journal of Internal Medicine*, 8(19); 561-567, 2008.
Han, et al., "Hepatoprotective Effect of Lactic Acid Bacteria, Inhibitor of β-Glucoronidase Production Against Intestinal Microflora," *Arch Pharm Res*, 2005, 28(3):325-329.
Office Action Issued in Corresponding Chinese Patent Application No. 201380041126.7, dated Dec. 3, 2019.
Yang, et al., "Ethanol Metabolism by Probiotic Lactic Acid Bacteria in Vivo," Proceeding of 2004 Joint Annual Meeting, American Dairy Science Association, American Society of Animal Science, Poultry Science Association, p. 384, 2004.

* cited by examiner

| Projected BAC | Actual BAC | Time |
|---|---|---|
| 0.036 | 0.036 | 9:32 |
| 0.04 | 0.04 | 9:52 |
| 0.052 | 0.052 | 10:12 |
| 0.079 | 0.079 | 10:32 |
| 0.085 | 0.085 | 10:52 |
| 0.085 | 0.086 | 11:12 |
| 0.08 | 0.072 | 11:32 |
| 0.074 | 0.068 | 11:52 |
| 0.069 | 0.067 | 12:12 |
| 0.063 | 0.058 | 12:32 |
| 0.057 | 0.052 | 12:52 |
| 0.052 | 0.048 | 1:12 |

COMPOSITIONS AND METHODS FOR REDUCING BLOOD ALCOHOL CONTENT

CROSS REFERENCE TO RELATED APPLICATIONS

This application is a continuation from U.S. application Ser. No. 14/850,165 filed Sep. 10, 2015, which is a continuation from U.S. application Ser. No. 13/796,692, filed Mar. 12, 2013, which claims priority of U.S. Application No. 61/679,308 filed Aug. 3, 2012, and U.S. Application No. 61/691,900 filed Aug. 22, 2012, each of which is specifically incorporated herein by reference in its entirety without disclaimer.

BACKGROUND OF THE INVENTION

A. Field of the Invention

The invention generally relates to methods and compositions for reducing blood alcohol content (BAC) in a subject after the subject has consumed alcohol.

B. Description of Related Art

Alcohol consumption is common, with the average adult consuming 5 liters of pure alcohol each year. Acute alcohol intoxication can result in low blood pressure, nausea, vomiting, memory loss, behavioral changes, dizziness, loss of motor skills, confusion, coma, and death. Long-term alcohol overconsumption can cause cardiovascular disease, malabsorption, chronic pancreatitis, alcoholic liver disease, cancer, nervous system damage, alcoholic lung disease, kidney stones, sexual dysfunction, hormonal imbalance, diabetes, rheumatoid arthritis, osteoporosis, skin disorders, brain damage, and birth defects.

Alcohol is absorbed throughout the gastrointestinal tract into the bloodstream. The blood alcohol concentration (BAC) reflects the amount of alcohol in the bloodstream. Alcohol that has been consumed is eliminated in a process that involves alcohol dehydrogenase (ADH) and acetaldehyde dehydrogenase, where the ADH converts alcohol to acetaldehyde, and the acetaldehyde dehydrogenase converts acetaldehyde to acetate. This alcohol elimination process is slow; it can take up to an hour for the body to eliminate the alcohol contained in each standard drink (i.e., 12 ounces of beer, 5 ounces of wine, or 1.5 ounces of 80-proof distilled spirits) that is consumed.

Probiotics are live microorganisms that are thought to be beneficial to a host organism. Lactic acid bacteria (such as members of the genus *Lactobacillus*) and bifidobacteria (such as members of the genus *Bifidobacterium*) are commonly used as probiotics and may aid in improving gastrointestinal health, preventing cancer, lowering cholesterol, reducing blood pressure, improving immune function, and decreasing inflammation.

Some studies have focused on using probiotics to alleviate hangover symptoms, prevent long-term liver damage caused by chronic alcohol consumption, or minimize the increase in BAC that follows alcohol consumption. See U.S. Pat. No. 7,544,356; U.S. Patent Pub. 2006/0263385. One unsolved aspect, however, is how to rapidly and effectively reduce blood alcohol content in a subject that currently has an elevated blood alcohol content.

SUMMARY OF THE INVENTION

The inventors have solved the problems associated with the length of time that it typically takes to reduce the BAC in a subject. In particular, the inventors have discovered methods and compositions that are surprisingly effective at rapidly reducing the BAC of a subject after the subject has consumed alcohol. For example, use of the disclosed compositions and methods can provide a 10-60% decrease in a subject's BAC in 5-60 minutes. The disclosed methods and compositions also decrease symptoms of intoxication in a subject who is experiencing such intoxication symptoms after consumption of alcohol.

The disclosed methods and compositions include the use of probiotics. It is not necessary to allow the probiotics to colonize in the gastrointestinal tract of the subject. Also, it is not necessary to consume the probiotics prior to alcohol consumption. Rather, the methods and compositions of the present invention can be used after alcohol has been consumed, with immediate effects on the BAC in a subject. It was further discovered that including NAD+ (along with the probiotics) in the methods and compositions provides a surprisingly rapid decrease in a subject's BAC.

In some embodiments, there are disclosed methods and compositions that aid in reducing the blood alcohol content in a subject using *Bifidobacterium*, *Lactobacillus*, and NAD+. NAD+ for use in the disclosed compositions and methods may be obtained from any of the many commercially available sources for NAD+. The NAD+ may be purified, or substantially purified, or it may be provided in a composition that includes additional ingredients. In the disclosed methods and compositions, the amount of NAD+ that is used may be 2, 3, 4, 5, 6, 7, 8, 9, 10, 11, 12, 13, 14, 15, 16, 17, 18, 19, 20 mg, or more, or any quantity derivable therein. In some aspects, the amount of NAD+ that is used is 5-15 mg, or the amount of NAD+ that is used is 10 mg.

*Lactobacillus* for use in the disclosed compositions and methods may be obtained from any of the many commercially available sources for *Lactobacillus*. The *Lactobacillus* may be purified, or substantially purified, from other probiotics and ingredients, or it may be provided in a composition that includes additional probiotics and/or ingredients. In the disclosed methods and compositions, the amount of *Lactobacillus* that is used may be 0.1, 0.2, 0.3, 0.4, 0.5, 0.6, 0.7, 0.8, 0.9, 1, 2, 3, 4, 5, 10, 15, 20, 25, 30, 35, 40, 45, 50, 55, 60, 65, 70, 75, 80, 85, 90, 95, 100, 125, 150 billion colony forming units (cfu) or cells, or more, or any quantity derivable therein. In particular embodiments, the amount of *Lactobacillus* that is used is 25-100 billion cfu of 50-75 billion cfu.

Any species or strain of *Lactobacillus* of lactic acid bacteria may be used in the disclosed compositions and methods. For example, in some embodiments, the *Lactobacillus* comprises *Lactobacillus* GG, *L. acidophilus*, *L. bulgaricus*, *L. jugurti*, *L. helveticus*, *L. salivarius*, *L. casei*, *L. plantarum*, *L. salivarius*, *L. rhamnosus*, *L. paracasei*, *L. lactis*, *L. infantis*, and/or *L. brevis*. In some aspects, the *Lactobacillus* comprises *Lactobacillus* GG, *L. acidophilus*, *L. casei*, *L. plantarum*, *L. salivarius*, *L. rhamnosus*, and/or *L. brevis*. It is expected that any strain in any species of *Lactobacillus* may be used in the disclosed compositions and methods. For example, if *L. acidophilus* is used, the *L. acidophilus* may comprise *L. acidophilus* DDS-1. In some embodiments, the species of strain of *Lactobacillus* comprises *Lactobacillus* GG, *L. acidophilus* DDS-1, *L. casei*, *L. plantarum*, *L. salivarius*, *L. rhamnosus*, and/or *L. brevis*.

*Bifidobacterium* for use in the disclosed compositions and methods may be obtained from any of the many commercially available sources for *Bifidobacterium*. The *Bifidobacterium* may be purified, or substantially purified, from other probiotics and ingredients, or it may be provided in a composition that includes additional probiotics and/or ingredients. In the disclosed methods and compositions, the amount of *Bifidobacterium* that is used may be 0.1, 0.2, 0.3, 0.4, 0.5, 0.6, 0.7, 0.8, 0.9, 1, 2, 3, 4, 5, 10, 15, 20, 25, 30, 35, 40, 45, 50, 55, 60, 65, 70, 75, 80, 85, 90, 95, 100, 125, 150 billion colony forming units (cfu) or cells, or more, or any quantity derivable therein. In particular embodiments, the amount of *Bifidobacterium* that is used is 25-100 billion cfu of 50-75 billion cfu.

Any species or strain of *Bifidobacterium* may be used in the disclosed compositions and methods. For example, in some embodiments, the *Bifidobacterium* comprises *Bifidobacterium* AN AHP 16467, *B. thermophilum, B. indicum, B. asteroids, B. lactis, B. longum, B. coagulans, B. dentium, B. infantis*, and/or *B. bifidum*. In some aspects, the *Bifidobacterium* comprises *Bifidobacterium* AN AHP 16467, *B. lactis, B. longum, B. infantis*, and/or *B. bifidum*. In other aspects, the *Bifidobacterium* comprises *B. lactis, B. longum, B. infantis*, and/or *B. bifidum*. It is expected that any strain in any species of *Lactobacillus* may be used in the disclosed compositions and methods.

In one aspect of the invention, there is disclosed a method of reducing blood alcohol content in a subject having an elevated blood alcohol content, the method comprising: providing an effective amount of *Bifidobacterium* to the subject, providing an effective amount of *Lactobacillus* to the subject, and providing an effective amount of NAD+ to the subject, wherein the subject's blood alcohol content is reduced. As used herein, an "elevated blood alcohol content" or "elevated BAC" includes a BAC of 0.02 or higher. For example, the BAC may be 0.02, 0.03, 0.04, 0.05, 0.06, 0.07, 0.08, 0.09, 0.10, 0.011, 0.12, 0.13, 0.14, 0.15, 0.16, 0.17, 0.18, 0.19, 0.20, or higher, or any BAC score derivable therein.

In the disclosed methods, the NAD+ may be provided to the subject before the *Lactobacillus* and *Bifidobacterium* are provided to the subject. For example, the NAD+ may be provided to the subject 5, 10, 15, 20, 25, 30, 35, 40, 45, 50, 55, 60 minutes, or more, or any quantity derivable therein, before the *Lactobacillus* and *Bifidobacterium* are provided to the subject. In certain aspects, the NAD+ is provided to the subject 10-50 minutes or 20-40 minutes before the *Lactobacillus* and *Bifidobacterium* are provided to the subject.

In other aspects, the *Lactobacillus* and/or *Bifidobacterium* may be provided to the subject before the NAD+ is provided to the subject. For example, the *Lactobacillus* and/or *Bifidobacterium* may be provided to the subject 5, 10, 15, 20, 25, 30, 35, 40, 45, 50, 55, 60 minutes, or more, or any quantity derivable therein, before the NAD+ is provided to the subject. In certain aspects, the *Lactobacillus* and/or *Bifidobacterium* is provided to the subject 10-50 minutes or 20-40 minutes before the NAD+ is provided to the subject.

In yet other aspects of the disclosed methods, the *Lactobacillus, Bifidobacterium*, and NAD+ are provided to the subject at the same time. For example, the *Lactobacillus, Bifidobacterium*, and NAD+ may be provided to the subject in a single composition. Alternatively, in any of the disclosed methods, the *Lactobacillus, Bifidobacterium*, and NAD+ may be provided to the subject in two or more compositions that are provided over a period of 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60 minutes, or more, or any quantity derivable therein. When a subject is provided NAD+, *Lactobacillus*, and *Bifidobacterium*, the NAD+, *Lactobacillus*, and *Bifidobacterium* may be provided to the subject in one, two, three, four, five, or more doses.

In some embodiments of the disclosed methods, the subject's blood alcohol content is reduced by 5, 10, 15, 20, 25, 30, 35, 40, 45, 50, 55, 60, 65, 70, 75, 80, 85, 90, 95%, or more, or any number derivable therein. For example, the subject's BAC is reduced by 10-50% within 10-40 minutes after providing NAD+, *Lactobacillus*, and *Bifidobacterium* to the subject. In other aspects, the subject's BAC is reduced by 20-40% within 20 minutes after providing NAD+, *Lactobacillus*, and *Bifidobacterium* to the subject.

In addition to the *Bifidobacterium, Lactobacillus*, and NAD+, the disclosed methods and compositions may further include zinc, vitamin B, n-acetyl cysteine, *Stevia* extract, D-Ribose, glutathione, iron, L-glutamine, liquid oxygen, and/or fructose. For example, zinc and/or vitamin B may be included. As a further example, in some of the disclosed compositions and methods, *Lactobacillus, Bifidobacterium*, NAD+, vitamin E, and vitamin B are included. When vitamin B is included in the disclosed methods and compositions, the vitamin B may include vitamin B-3, vitamin B-5, vitamin B-6, and/or vitamin B-12.

In some aspects, the disclosed methods and compositions include an antioxidant, which may be, for example L-carnosine, a carotenoid, lutein, lycopene, zeaxathin, Coenzyme Q10, green tea, selenium, soy, an isoflavone, vitamin A, vitamin C, vitamin E, and/or alpha-lipoic acid. For example, the antioxidant may be Coenzyme Q10 and/or vitamin E. When a carotenoid is included in the disclosed methods and compositions, the carotenoid may be beta-carotene, alpha-carotene, gamma-carotene, and/or beta-cryptoxanthin.

In some aspects, there is provided a composition that includes *Bifidobacterium, Lactobacillus*, NAD+, vitamin E, and vitamin B. In other aspects, there is provided a composition that includes *Bifidobacterium, Lactobacillus*, NAD+, vitamin E, vitamin B, zinc, and Coenzyme Q10. Such compositions may be used in any of the disclosed methods or in combination with any of the other ingredients described herein.

The disclosed compositions may be in liquid form, semi-solid form, solid form, chewable form, or one or more pills, capsules or tablets. In the disclosed methods, one or more compositions may be used, and one or more of the compositions that are used may be in liquid form, semi-solid form, solid form, chewable form, or one or more pills, capsules or tablets.

Also provided are methods of identifying probiotics that can rapidly reduce BAC in a subject. Such probiotics that are useful in the disclosed compositions and methods may be those probiotics that can survive and function in the human digestive tract; function in First Pass Metabolism; function in the aerodigestive tract, intranasal systemic pathway, or intranasal brain pathway; and/or provide significant alcohol dehydrogenase activity (such as provided by one or more of ADH1-7). Such probiotics may be tested for suitability for use in the disclosed compositions and methods by allowing subjects to voluntarily consume alcohol and then to voluntarily ingest the probiotics (with or without additional ingredients, such as those described herein) at a time when the subject is feeling the effects of alcohol consumption or is experiencing alcohol intoxication. Suitability of the probiotics can be assessed by measuring the subject's BAC over time and comparing the subject's actual BAC score following administration of the probiotics to a projected BAC score (which provides an expected BAC score for the subject absent administration of the probiotics and can be calculated using any of the different tools known in the art). Particular probiotics that may be tested in such a manner and that may be useful in the disclosed methods and compositions include the following groups/genera: *Leuconostoc* (including *L. mesenteroides, L. citrovorum*), *Pediococcus*, Anaerobic *Streptococci, Peptococcus, Peptostreptococcus, Ruminococcus, Coprococcus*, Sarcina, Bacillaceae (including *B. Subtilis* and *B. cereus*), *Clostridium* (including *C. perfrigens, C. butyricum*, and *C. botulinum*), *Propionibacteriacea* (including *P. acnes*), *Eubacterium* (including *E. aerofaciens* and *E. rectal*), and *Saccharomyces* (including *S. boulardii*).

Also provided are methods of identifying additional factors that can rapidly reduce BAC in a subject. For example, recombinant or isolated ADH enzymes (e.g., ADH-7 and other members of the ADH IV family) may be tested for suitability for use in the disclosed compositions and methods as described above.

In the provided methods, compositions may be administered in any suitable manner that delivers the composition to a location in the body where alcohol is located. For example, the compositions may be administered orally. Similarly, the compositions may be formulated in any manner that allows administration to a location in the body where alcohol is located. For example, the compositions may be formulated for oral administration, such as, for example, in liquid form, semi-solid form, solid form, chewable form, a pill, a capsule, a tablet, or a powder.

Unless otherwise specified, the percent values expressed herein are weight by weight and are in relation to the total composition.

Throughout this application, the term "about" is used to indicate that a value includes the inherent variation of error for the device obtaining the value, the method being employed to determine the value, or the variation that exists among the objects being evaluated.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. With respect to the transitional phase "consisting essentially of," in one non-limiting aspect, a basic and novel characteristic of the compositions and methods disclosed in this specification includes the composition's ability to rapidly effectuate a reduction in BAC in a subject.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF ILLUSTRATIVE EMBODIMENTS

Figure 1:
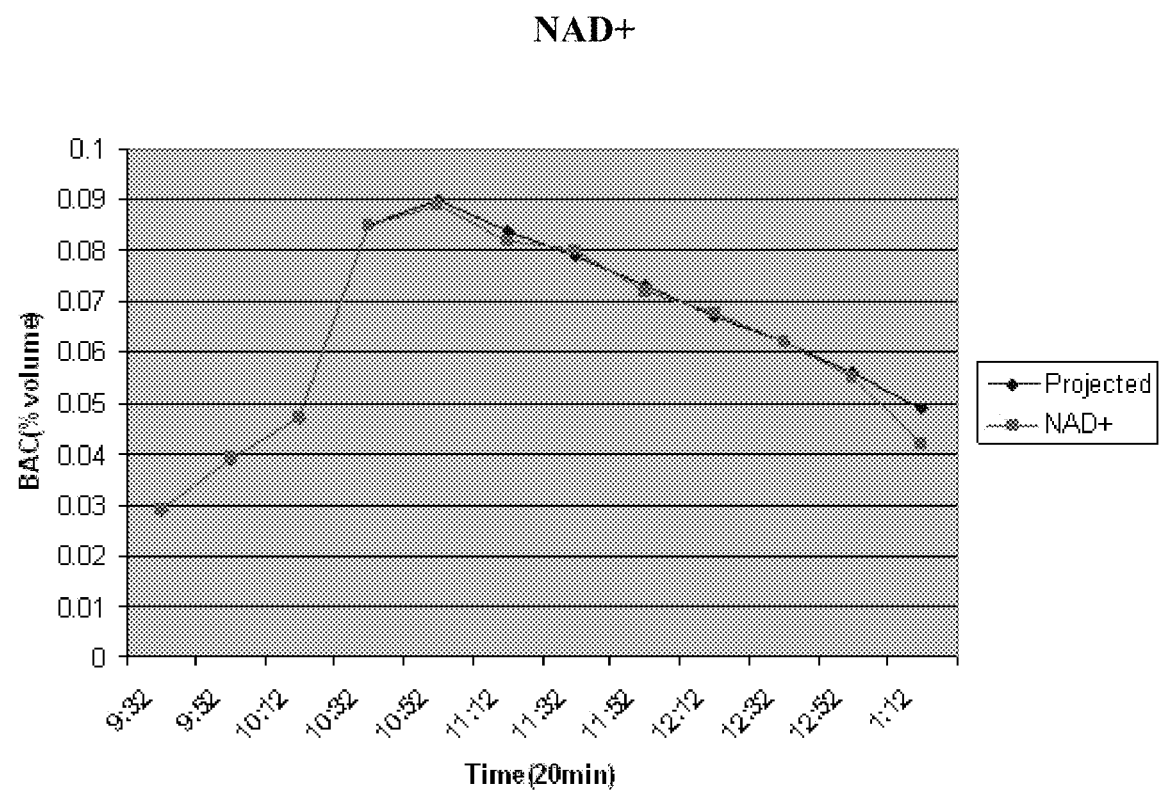
FIG. 1. A graph showing projected and actual BAC scores for a subject before and after administration of NAD+. NAD+ was administered at the time point labeled 10:52.

Alcohol consumption often occurs at many social functions ranging from birthday parties, retirement parties, spectator sporting events, work-related functions, lunches, dinners, conferences, and the like. This can result in instances where a person's BAC is at a level that impairs speech and coordination. The typical solution in such situations is to wait for relatively long periods of time for the BAC to decrease and for the person to recover from the effects of alcohol consumption. Given today's time constraints on a person's schedule, waiting for the BAC to come down may not be an acceptable option.

The present invention solves these problems by safely and rapidly reducing the BAC in a subject. In particular, the inventors discovered that a combination of probiotics alone or in further combination with NAD+ works synergistically to reduce the BAC of a subject when the ingredients are orally ingested after the subject has consumed alcohol. Without wishing to be bound by theory, the inventors hypothesize that the synergistic results achieved by the disclosed methods and compositions involve increased First Pass Metabolism (FPM) of alcohol and improved elimination of acetaldehyde. Moreover, because the disclosed compositions and methods are surprisingly effective at rapidly reducing BAC with test subjects reporting a highly accelerated recovery from the effects of alcohol consumption, the inventors hypothesize that an additional pathway may be involved that eliminates alcohol vapors and/or prevents alcohol vapor absorption in the aerodigestive tract, intranasal systemic pathway, or intranasal brain pathway.

These and other aspects of the invention are discussed in further detail in the following non-limiting subsections.

A. Compositions

Compositions are disclosed for rapidly reducing BAC in a subject after the subject has consumed alcohol. Such compositions may include one or more sources of probiotics (such as members of the *Lactobacillus* genus and members of the *Bifidobacterium* genus) and one or more sources of NAD+.

1. *Bifidobacterium*

*Bifidobacterium* is a genus of Gram-positive, non-motile, often branched anaerobic bacteria. They are found in mammals in the gastrointestinal tract, vagina, and mouth. *Bifidobacterium* is one of the major genera of bacteria that make up the colon flora in mammals. *Bifidobacterium* organisms are commercially available and sold as probiotics for human consumption. For example, Complete Probiotics capsules by Dr. Mercola® contain 70 billion organisms including three species of *Bifidobacterium*. Other commercial sources of *Bifidobacterium* are also available (e.g., Align® Bifantis® *Bifidobacterium infantis* 35624).

*Bifidobacterium* AN AHP 16467 is one strain of *Bifidobacterium* that may be used in the disclosed methods and compositions. However, any species of *Bifidobacterium* may be suitable because strains in this genus are known to live and function in the human digestive tract and have been shown to be safe for human consumption. Such strains that are useful in the disclosed methods and compositions include, but are not limited to *B. infantis, B. breve, B. adolescentis, B. animalis, B. pseudolongum, B. thermophilum, B. indicum, B. asteroids, B. lactis, B. longum, B. coagulans, B. dentium, B. infantis*, and *B. bifidum*.

2. *Lactobacillus*

*Lactobacillus* is a genus of Gram-positive facultative anaerobic or microaerophilic rod-shaped bacteria. The genus makes up a major part of a group of bacteria (lactic acid bacteria) that convert lactose and other sugars to lactic acid. They are found in the gastrointestinal tract and vagina in humans. Some strains of *Lactobacillus* have potential therapeutic properties including anti-inflammatory and anti-cancer activities. There are a wide range of commercial sources for *Lactobacillus* (e.g., Health & Wellness 30-Capsules or Digestive Health 30-Capsules sold by Culturelle®, Cromwell, Conn.; Nutrition Now® Pro-Biotics *Acidophilus* from GNC; FoodScience® of Vermont *Lactobacillus Acidophilus* capsules).

*Lactobacillus* GG AN ATCC 531003 (also called *Lactobacillus* GG) is one strain of *Lactobacillus* that may be used in the disclosed methods and compositions. However, any species of *Lactobacillus* may be suitable because strains in this genus are known to live and function in the human digestive tract and have been shown to be safe for human consumption. Such strains that are useful in the disclosed methods and compositions include, but are not limited to *L. acidophilus* (e.g., *L. acidophilus* DDS-1, *L. acidophilus* LA-5, *L. acidophilus* NCFM), *L. bulgaricus, L. jugurti, L. helveticus, L. salivarius, L. casei, L. plantarum, L. salivarius, L. rhamnosus* (e.g., *L. rhamnosus* A), *L. paracasei, L. lactis, L. infantis*, and *L. brevis*.

3. NAD+ (Nicotinamide Adenine Dinucleotide)

ADH enzymes catalyze the oxidation of ethanol into acetaldehyde in a reaction that uses nicotinamide adenine dinucleotide (NAD+). The reaction results in conversion of ethanol and NAD+ to acetaldehyde and NADH. ALDH enzymes convert aldehydes into carboxylates by oxidation, and this reaction also requires NAD+.

NAD+ can be provided by any means known in the art, such as administration of purified or substantially purified NAD+, or administration of a composition that includes NAD+. Commercially available sources are abundant (e.g., Liquid CoQ10 Orange Flavor, sold by NOW® Foods, Bloomingdale, Ill.; NAD 25 mg lozenges sold by NOW® Foods, Bloomingdale, Ill.). In addition, NAD+ may be provided by administration of an agent that increases NAD+ levels in the body, is a precursor of NAD+, is a component in a reaction pathway that creates NAD+, or is involved in a reaction in which NADH or NADP are converted to NAD+. For example, the disclosed compositions and methods may include L-glutamine or niacin (vitamin B3). The disclosed compositions and methods may also include ubiquinone and NADH because ubiquinone accepts electrons in a reaction that converts NADH to NAD+ and ubiquinone.

4. Additional Ingredients

The compositions of the present invention may comprise various additional ingredients, including zinc, vitamin B (e.g., vitamin B-3, vitamin B-5, vitamin B-6, vitamin B-12), n-acetyl cysteine, *Stevia* extract (e.g., *Stevia rebaudiana*), D-Ribose, liquid oxygen, iron, fructose, and/or glutathione.

Antioxidants may be included in the disclosed methods and compositions. Useful antioxidants include, but are not limited to, L-carnosine, carotenoids (e.g., beta-carotene, alpha-carotene, gamma-carotene, and beta-cryptoxanthin), lutein, lycopene, zeaxathin, Coenzyme Q10, green tea, selenium, soy, isoflavones, vitamins A, B, C, and E, and/or alpha-lipoic acid.

Other useful ingredients include preservatives or components that provide a desirable flavor, color, consistency, or pH to the composition.

The compositions of the present invention may be packaged in any package configuration suitable for products that are orally administered. Non-limiting examples for such products include capsules, bottles, tubes, jars, pouches, and packets. The packages may be configured for single-use (one dose) or multiple-use administration. The composition may be provided in liquid form, semi-solid form, solid form, chewable form, a pill, a capsule, a tablet, or a powder.

The compositions of the present invention may also be sterile. They may be sterilized via an aseptic manufacturing process or sterilized after packaging by methods known in the art.

5. Preparation

The compositions of the present invention may be prepared by suitable methods known to one of skill in the art for ingestible products. For example, and as noted above, the probiotic and NAD+ components useful in the disclosed methods and compositions can be obtained from commercial sources. As one non-limiting example, NAD+ is available in Liquid CoQ10, which is made by NOW® Foods and contains 5 mg NAD+ in a 5 mL dose. In another non-limiting example, *Lactobacillus* is provided in Culturelle® Health & Wellness capsules, which contain *Lactobacillus* GG. *Lactobacillus* and *Bifidobacterium* may also be provided in Dr. Mercola's® Complete Probiotics capsules, each of which contains 35 billion cells including the following species: *Lactobacillus acidophilus* DDS-1, *Lactobacillus casei, Lactobacillus plantarum, Lactobacillus salivarius, Lactobacillus rhamnosus, Lactobacillus brevis, Bifidobacterium lactis, Bifidobacterium longum, Bifidobacterium bifidum*, and *Streptococcus thermophilus*. Alternatively, *Bifidobacterium* may be provided as one or more capsules of Align® Bifantis® *Bifidobacterium infantis* 35624.

B. Methods of Use

The disclosed compositions may be used in methods of reducing the BAC in a subject, such as a human subject, that has consumed alcohol. The composition may be administered in one dose, or in multiple doses. The components of the composition may be administered at the same time, or one or more components may be administered before one or more of the other components.

The composition should preferably be ingested after the subject has consumed alcohol. For example, the composition may be consumed 5-10, 10-20, 20-30, 30-40, 40-50, 50-60, 60-70, 70-80, 80-90, 90-100, 100-110, 110-120 minutes or more, or any integer derivable therein, after alcohol has been consumed. The composition may be ingested at a time when the subject is experiencing effects of alcohol consumption or alcohol intoxication. The composition may be ingested after a subject's BAC level is 0.01, 0.02, 0.03, 0.04, 0.05, 0.06, 0.07, 0.08, 0.09, 0.1, 0.2, 0.3, 0.4, or more. The composition may be ingested after a subject has consumed 1, 2, 3, 4, 5, 6, 7, 8, 9, 10, or more drinks.

EXAMPLES

The following examples are included to demonstrate certain non-limiting aspects of the invention. It should be appreciated by those of skill in the art that the techniques disclosed in the examples that follow represent techniques discovered by the applicants to function well in the practice of the invention. However, those of skill in the art should, in light of the present disclosure, appreciate that many changes can be made in the specific embodiments that are disclosed and still obtain a like or similar result without departing from the spirit and scope of the invention.

Example 1

The following experiments involved subjects who voluntarily consumed alcoholic beverages. The subjects chose the type and amount of alcohol that was consumed, as well as the rate at which the alcohol was consumed. At the point when the subjects started to feel effects of their alcohol consumption and chose to stop consuming alcohol, the subjects voluntarily consumed a composition that contained a source of NAD+, *Lactobacillus, Bifidobacterium*, or a combination of two or more of those ingredients. Projected BAC scores were calculated approximately every twenty minutes using an online BAC calculator provided by the Wisconsin Department of Transportation, which provides a projected BAC based on factors such as the subject's weight, sex, alcohol consumed, rate of alcohol consumed, and food consumed. BAC scores were also quantitatively measured approximately every twenty minutes using a breathalyzer. The projected BAC score served as a negative control because it estimates the change in BAC that is expected to occur over time after a subject stops consuming alcohol. Changes in each subject's behavior were also observed over the course of the experiment.

The ingredients that were administered to the subjects are commercially available and sold for human consumption. In the following experiments, NAD+ was provided by administering 5 mL of Liquid CoQ10, which is made by NOW Foods and contains 5 mg NAD+ in the 5 mL dose. To administer *Lactobacillus*, the subjects were given two Culturelle® Health & Wellness capsules, each of which contains *Lactobacillus* GG (10 billion cells). To administer *Bifidobacterium*, subjects were given two capsules of Align® Bifantis® *Bifidobacterium infantis* 35624, which contain 1 billion cfu per capsule. To administer *Lactobacillus* and *Bifidobacterium*, subjects were given 1-2 capsules of Dr. Mercola's® Complete Probiotics capsules, each of which contains 35 billion cells including the following species: *Lactobacillus acidophilus* DDS-1, *Lactobacillus casei, Lactobacillus plantarum, Lactobacillus salivarius, Lactobacillus rhamnosus, Lactobacillus brevis, Bifidobacterium lactis, Bifidobacterium longum, Bifidobacterium bifidum*, and *Streptococcus thermophilus*. Subjects were also given 5 mg of zinc, which was provided in liquid form.

As the following experiments show, administration of NAD+, *Lactobacillus*, or *Bifidobacterium* had no effect or only a minimal effect on the subject's BAC score. In other words, the subject's actual BAC score following administration of NAD+, *Lactobacillus*, or *Bifidobacterium* was similar to the subject's projected BAC score over the course of the experiment. Thus, any reduction in BAC score was due to the passage of time, and not due to the administration of NAD+, *Lactobacillus*, or *Bifidobacterium*. In contrast, for subjects that received a combination of NAD+, *Lactobacillus*, and *Bifidobacterium*, the subject's BAC was dramatically reduced as compared to the subject's projected BAC.

In general, the subject's BAC was reduced by 15-60% within 5-60 minutes following administration of NAD+, *Lactobacillus*, and *Bifidobacterium*. For example, in one experiment, the subject's BAC was reduced 34% (0.12 BAC to 0.079 BAC) within eight minutes of receiving a combination of NAD+, *Lactobacillus*, and *Bifidobacterium*. With NAD+ alone, *Lactobacillus* alone, or *Bifidobacterium* alone, the subject's BAC decreased much more slowly (typically only 0-10% in a 20 minute period). Moreover, the data show that most subjects receiving NAD+ alone, *Lactobacillus* alone, or *Bifidobacterium* alone exhibited an increase in BAC twenty minutes after administration, while subjects receiving the combination of NAD+, *Lactobacillus*, and *Bifidobacterium* exhibited a marked decrease in BAC twenty minutes after administration. The observed ability of NAD+, *Lactobacillus*, and *Bifidobacterium* to act synergistically to rapidly reduce a subject's BAC was surprising because of the minimal effects on BAC that were observed when NAD+ alone, *Lactobacillus* alone, or *Bifidobacterium* alone was administered.

In the experiment shown in FIG. 1, a male subject age 30 weighing 198 pounds consumed beer and wine. NAD+ was administered to the subject at the time point labeled 10:52 on the graph in FIG. 1. At that time point, the subject's BAC score was 0.089, and the subject exhibited signs of intoxication. Twenty minutes later, at the 11:12 time point, the subject's BAC score was 0.082 (with a projected BAC of 0.084), and the subject continued to exhibit signs of intoxication. As shown in FIG. 1, the NAD+ appeared to have no effect on the subject's BAC score in that there was no significant difference between the subject's actual and projected BAC scores following administration of NAD+.

Figure 2:
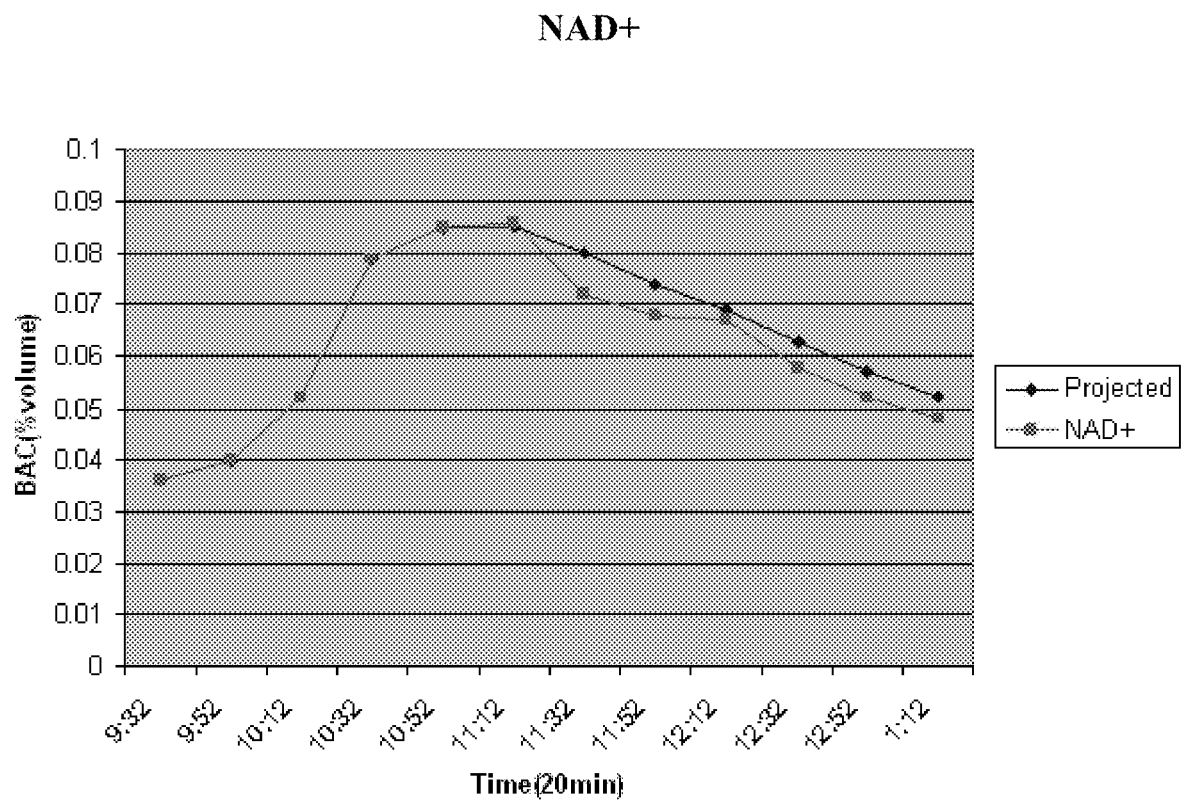
FIG. 2. A graph showing projected and actual BAC scores for a subject before and after administration of NAD+. NAD+ was administered at the time point labeled 10:52.

In the experiment shown in FIG. 2, a male subject age 29 weighing 188 pounds consumed beer. NAD+ was administered to the subject at the time point labeled 10:52 on the graph in FIG. 2. At that time point, the subject's BAC score was 0.085, and the subject exhibited signs of intoxication. Twenty minutes later, at the 11:12 time point, the subject's BAC score was 0.086 (with a projected BAC of 0.085), and the subject continued to exhibit signs of intoxication. As shown in FIG. 2, the NAD+ appeared to have minimal or no effect on the subject's BAC score in that there was no significant difference between the subject's actual and projected BAC scores following administration of NAD+.

Figure 3:
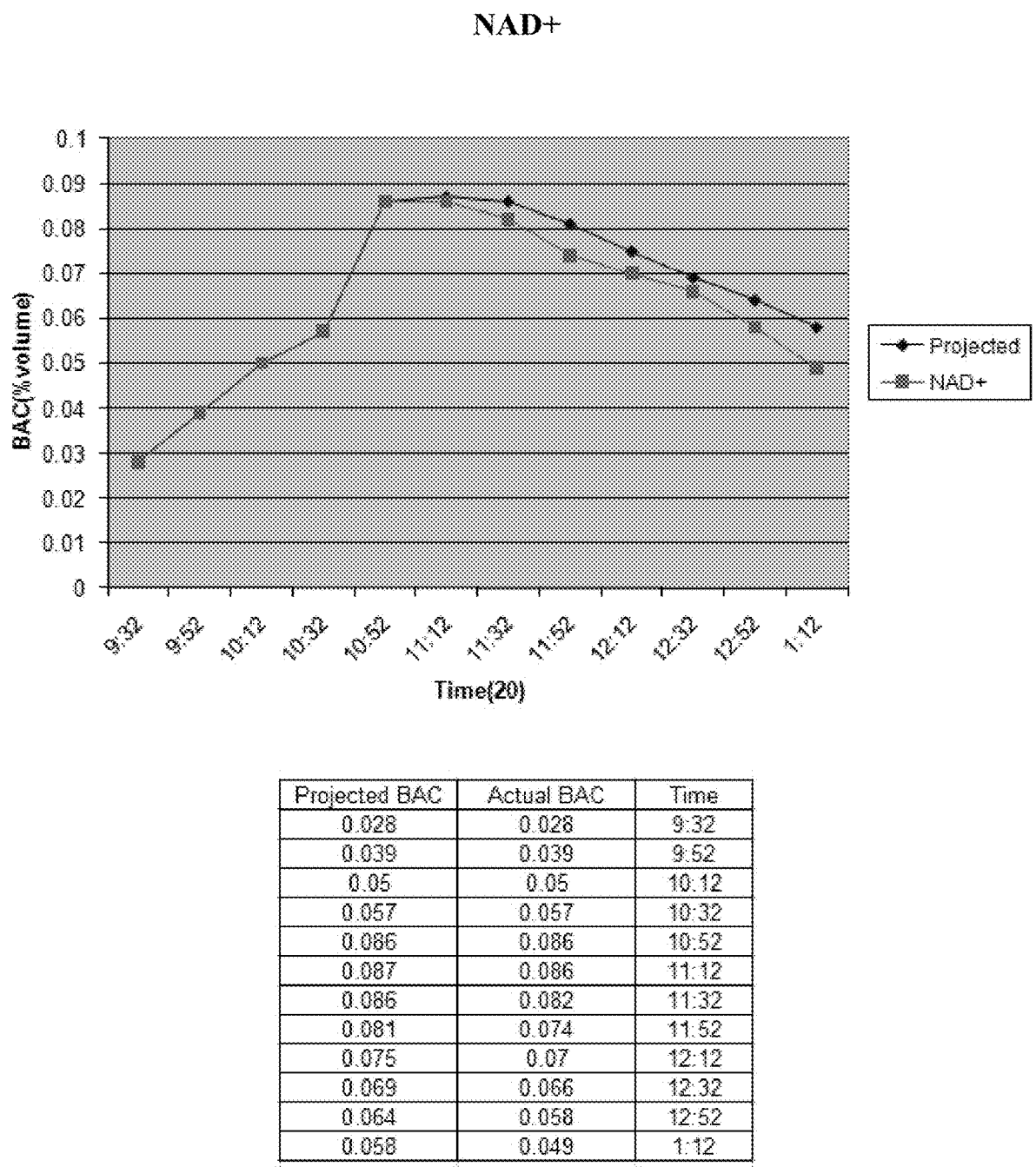
FIG. 3. A graph showing projected and actual BAC scores for a subject before and after administration of NAD+. NAD+ was administered at the time point labeled 10:52.

In the experiment shown in FIG. 3, a male subject age 28 weighing 169 pounds consumed beer and vodka. NAD+ was administered to the subject at the time point labeled 10:52 on the graph in FIG. 3. At that time point, the subject's BAC score was 0.086, and the subject exhibited signs of intoxication. Twenty minutes later, at the 11:12 time point, the subject's BAC score was 0.086 (with a projected BAC of 0.087), and the subject continued to exhibit signs of intoxication. As shown in FIG. 3, the NAD+ appeared to have little effect on the subject's BAC score in that there was little difference between the subject's actual and projected BAC scores following administration of NAD+.

Figure 4:
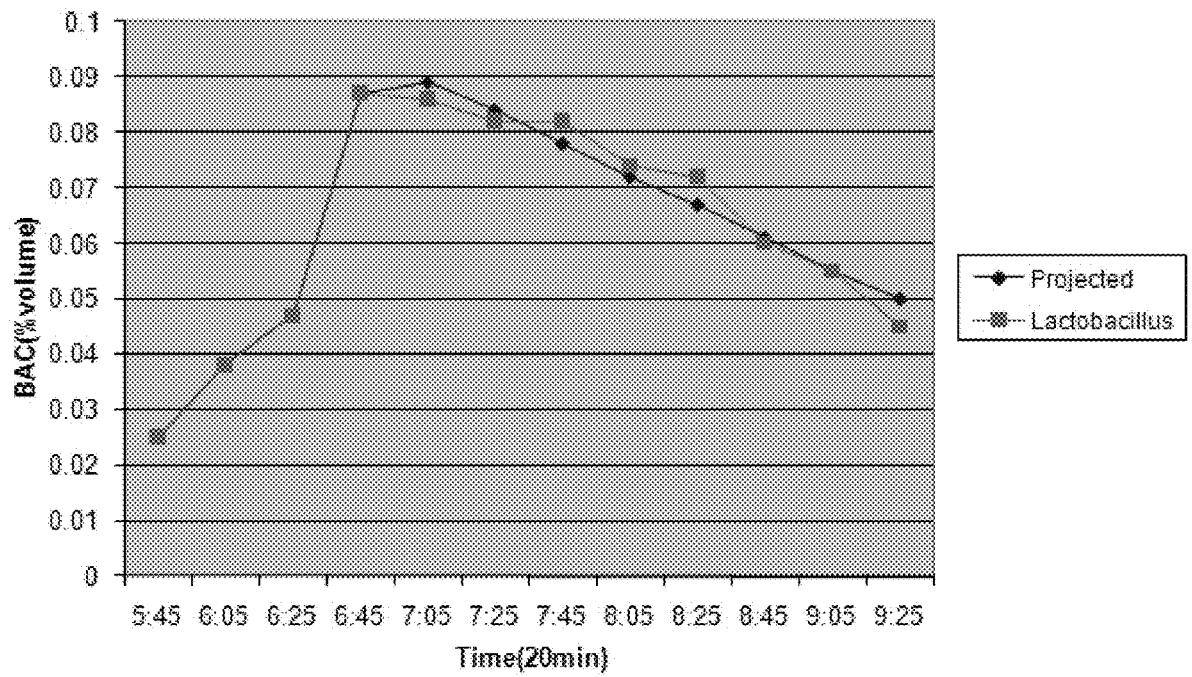
FIG. 4. A graph showing projected and actual BAC scores for a subject before and after administration of *Lactobacillus*. *Lactobacillus* was administered at the time point labeled 7:05.

In the experiment shown in FIG. 4, a female subject age 25 weighing 122 pounds consumed wine and vodka. *Lactobacillus* was administered to the subject at the time point labeled 7:05 on the graph in FIG. 4. At that time point, the subject's BAC score was 0.086, and the subject exhibited signs of intoxication. Twenty minutes later, at the 7:25 time point, the subject's BAC score was 0.082 (with a projected BAC of 0.084), and the subject continued to exhibit signs of intoxication, including loss of motor skills. As shown in FIG. 4, the *Lactobacillus* appeared to have no effect on the subject's BAC score in that there was no significant difference between the subject's actual and projected BAC scores following administration of *Lactobacillus*.

Figure 5:
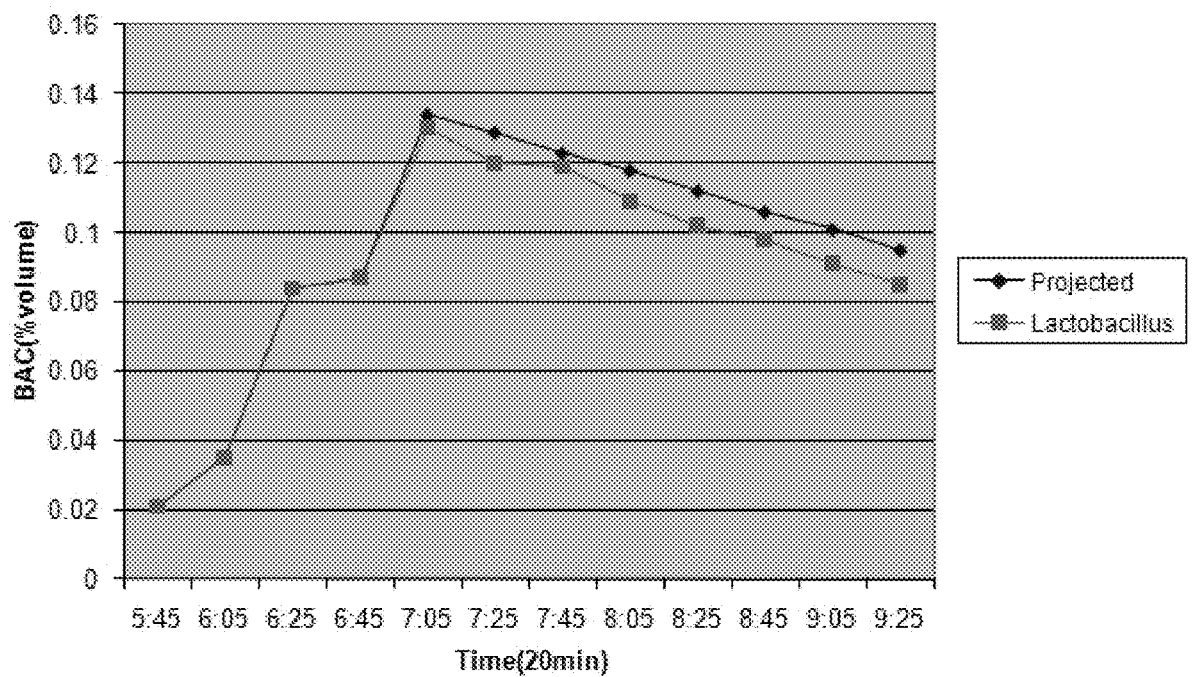
FIG. 5. A graph showing projected and actual BAC scores for a subject before and after administration of *Lactobacillus*. *Lactobacillus* was administered at the time point labeled 7:05.

In the experiment shown in FIG. 5, a male subject age 27 weighing 155 pounds consumed beer and wine. *Lactobacillus* was administered to the subject at the time point labeled 7:05 on the graph in FIG. 5. At that time point, the subject's BAC score was 0.13. Twenty minutes later, at the 7:25 time point, the subject's BAC score was 0.12 (with a projected BAC of 0.129). As shown in FIG. 5, the *Lactobacillus* appeared to have little effect on the subject's BAC score in that there was little difference between the subject's actual and projected BAC scores following administration of *Lactobacillus*.

Figure 6:
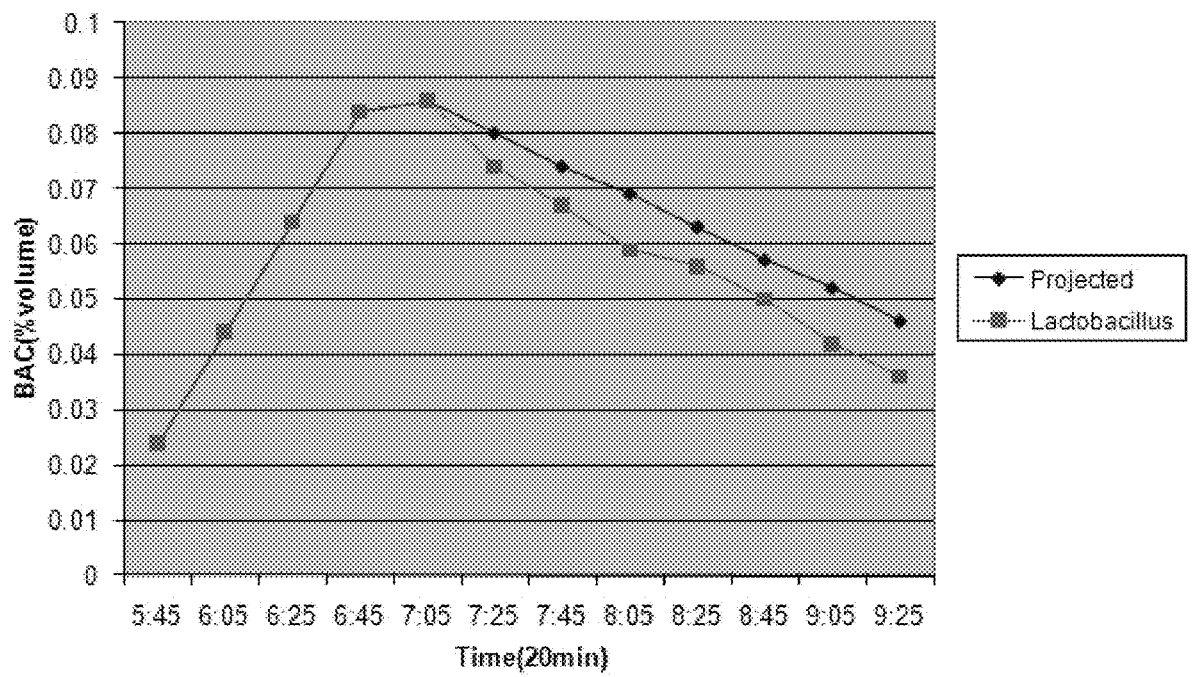
FIG. 6. A graph showing projected and actual BAC scores for a subject before and after administration of *Lactobacillus*. *Lactobacillus* was administered at the time point labeled 7:05.

In the experiment shown in FIG. 6, a male subject age 29 weighing 169 pounds consumed beer and vodka. *Lactobacillus* was administered to the subject at the time point labeled 7:05 on the graph in FIG. 6. At that time point, the subject's BAC score was 0.086, and the subject was exhibiting signs of intoxication, including glossy eyes and slurred speech. Twenty minutes later, at the 7:25 time point, the subject's BAC score was 0.067 (with a projected BAC of 0.074). As shown in FIG. 6, the *Lactobacillus* appeared to have little effect on the subject's BAC score in that curves illustrating the actual and projected BAC scores following administration of *Lactobacillus* were similar.

Figure 7:
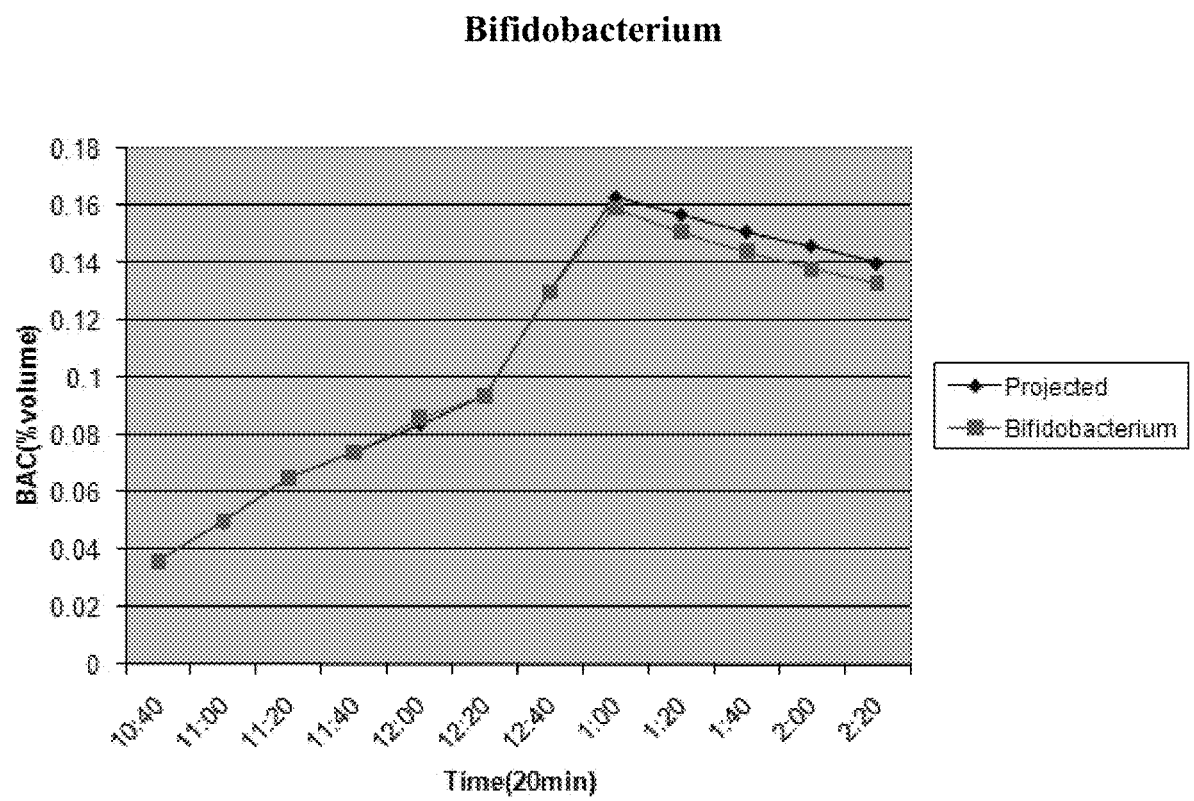
FIG. 7. A graph showing projected and actual BAC scores for a subject before and after administration of *Bifidobacterium*. *Bifidobacterium* was administered at the time point labeled 1:00.

In the experiment shown in FIG. 7, a female subject age 24 weighing 146 pounds consumed wine. *Bifidobacterium* was administered at the time point labeled 1:00 on the graph shown in FIG. 7. At that time point, the subject's BAC was 0.159, and the subject exhibited signs of intoxication. Twenty minutes later, at the 1:20 time point, the subject's BAC was 0.151 (with a projected BAC of 0.157). As shown in FIG. 7, the *Bifidobacterium* appeared to have little effect on the subject's BAC score in that there was little difference between the subject's actual and projected BAC scores following administration of *Bifidobacterium*.

Figure 8:
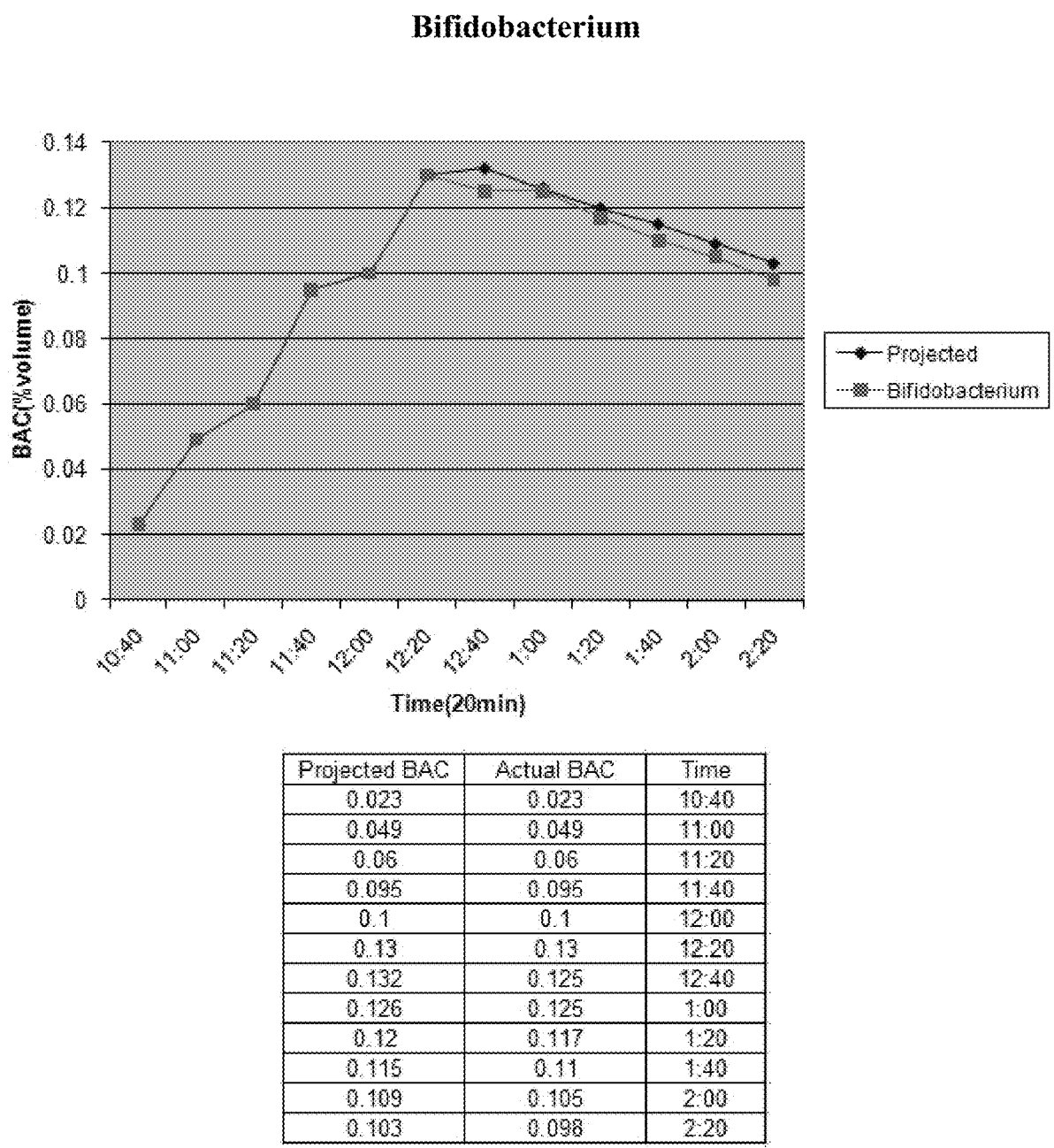
FIG. 8. A graph showing projected and actual BAC scores for a subject before and after administration of *Bifidobacterium*. *Bifidobacterium* was administered at the time point labeled 12:20.

In the experiment shown in FIG. 8, a male subject age 28 weighing 171 pounds consumed alcoholic beverages. *Bifidobacterium* was administered at the time point labeled 12:20 on the graph shown in FIG. 8. At that time point, the subject's BAC was 0.13, and the subject exhibited signs of intoxication, including loss of motor skills. Twenty minutes later, at the 12:40 time point, the subject's BAC was 0.125 (with a projected BAC of 0.132). As shown in FIG. 8, the *Bifidobacterium* appeared to have little effect on the subject's BAC score in that there was little difference between the subject's actual and projected BAC scores following administration of *Bifidobacterium*.

Figure 9:
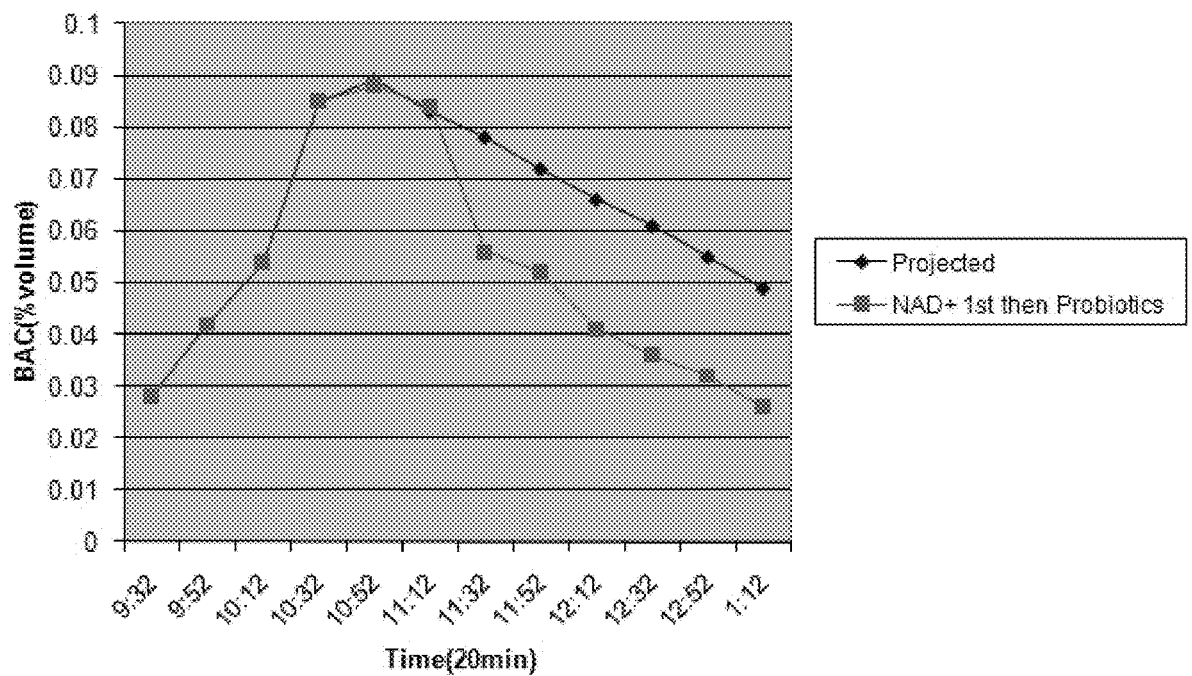
FIG. 9. A graph showing projected and actual BAC scores for a subject before and after administration of NAD+ followed by administration of *Lactobacillus* and *Bifidobacterium*. NAD+ was administered at the time point labeled 10:52, followed by administration of *Lactobacillus* and *Bifidobacterium* at the time point labeled 11:32.

In the experiment shown in FIG. 9, a male subject age 29 weighing 182 pounds consumed beer and vodka. NAD+ was administered at the time point labeled 10:52 (when the subject's BAC was 0.088), followed by administration of *Lactobacillus* and *Bifidobacterium* at the time point labeled 11:32 (when the subject's BAC was 0.056). Twenty minutes later, at the 11:52 time point, the subject's projected BAC was 0.072, but the subject's actual BAC was only 0.052. At the 12:32 time point, the subject's projected BAC was 0.061, but the subject's actual BAC was only 0.036. As shown in FIG. 9, the subject's actual BAC was greatly reduced as compared to the subject's projected BAC following administration of NAD+, *Lactobacillus*, and *Bifidobacterium*.

Figure 10:
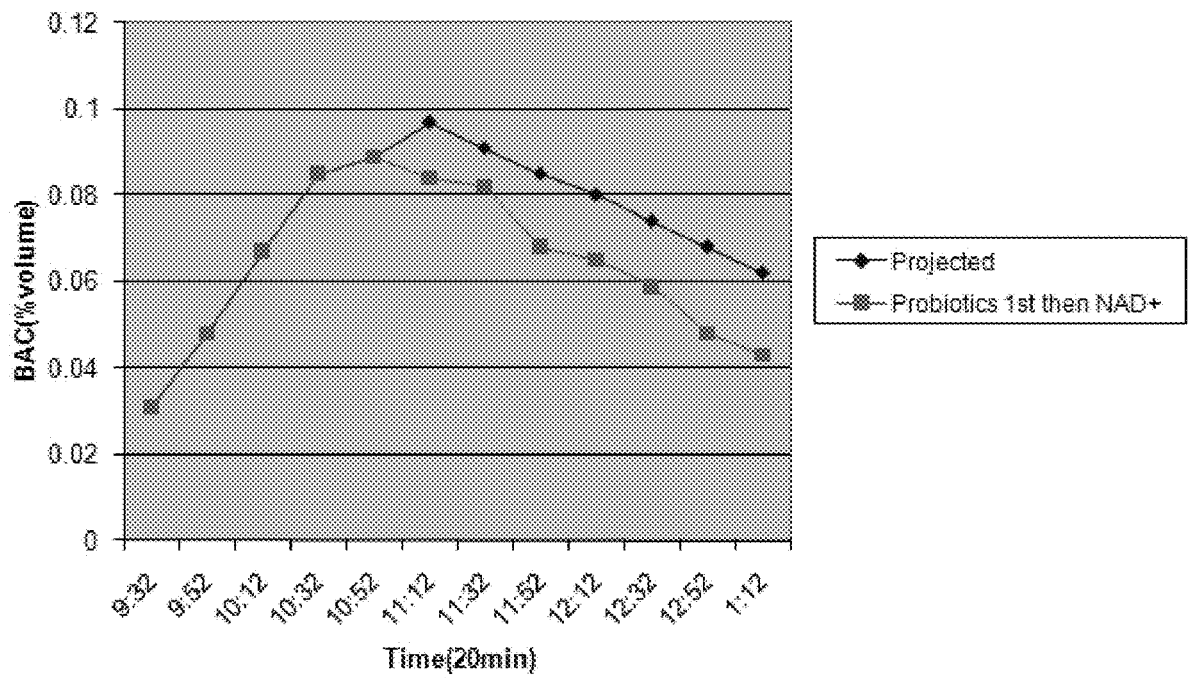
FIG. 10. A graph showing projected and actual BAC scores for a subject before and after administration of *Lactobacillus* and *Bifidobacterium* followed by administration of NAD+. *Lactobacillus* and *Bifidobacterium* were administered at the time point labeled 10:52, followed by administration of NAD+ at the time point labeled 11:32.

In the experiment shown in FIG. 10, a male subject age 30 weighing 195 pounds consumed wine and beer. *Lactobacillus* and *Bifidobacterium* were administered at the time point labeled 10:52 (when the subject's BAC was 0.089), followed by administration of NAD+ at the time point labeled 11:32 (when the subject's BAC was 0.082). Twenty minutes later, at the 11:52 time point, the subject's projected BAC was 0.085, but the subject's actual BAC was only 0.068. As shown in FIG. 10, the subject's actual BAC was greatly reduced as compared to the subject's projected BAC following administration of NAD+, *Lactobacillus*, and *Bifidobacterium*. Although some reduction in BAC was observed following administration of NAD+, the largest reduction in BAC occurred between the 11:32 and 11:52 time points, after the subject had ingested the *Lactobacillus*, and *Bifidobacterium* in addition to the NAD+. In the twenty minutes between the 11:32 and 11:52 time points, the subject's actual BAC was reduced by 17.1% with administration of NAD+, *Lactobacillus*, and *Bifidobacterium*, while the subject's BAC was projected to decrease by only 6.6% without administration of NAD+, *Lactobacillus*, and *Bifidobacterium*.

Figure 11:
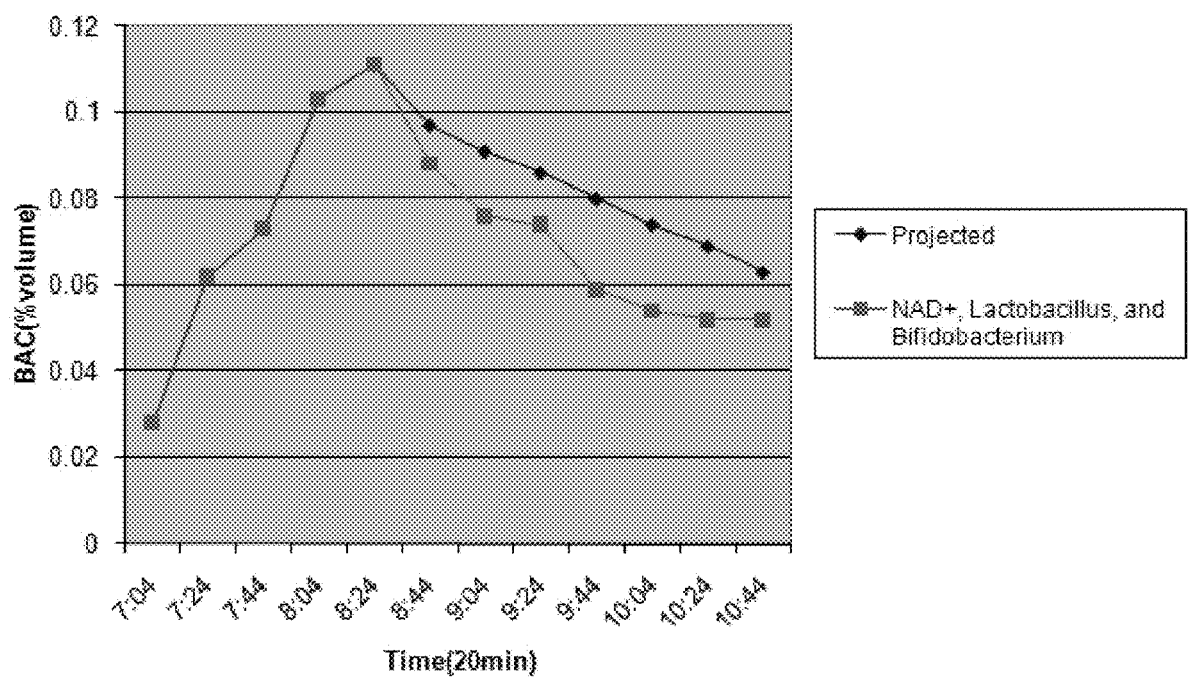
FIG. 11. A graph showing projected and actual BAC scores for a subject before and after administration of a composition comprising NAD+, *Lactobacillus*, and *Bifidobacterium*. The composition was administered at the time point labeled 8:24.

In the experiment shown in FIG. 11, a female subject age 80 weighing 135 pounds consumed beer. A composition comprising NAD+, *Lactobacillus*, and *Bifidobacterium* was administered at the time point labeled 8:24 (when the subject's BAC was 0.111). At that time point, the subject was exhibiting signs of intoxication, including blurred vision and loss of motor skills. Twenty minutes later, at the 8:44 time point, the subject's projected BAC was 0.097, but the subject's actual BAC was 0.088. At the 9:04 time point, the subject's projected BAC was 0.091, but the subject's actual BAC was 0.076, and the subject exhibited improved motor skills. At the 9:44 time point, the subject's projected BAC was 0.08, but the subject's actual BAC was only 0.059, and the subject did not exhibit signs of intoxication. As shown in FIG. 11, the subject's actual BAC was greatly reduced as compared to the subject's projected BAC following administration of NAD+, *Lactobacillus*, and *Bifidobacterium*. Between the 8:24 and 9:04 time points, the subject's actual BAC was reduced by 31.5% with administration of NAD+, *Lactobacillus*, and *Bifidobacterium*, while the BAC was projected to decrease by only 18% without administration of NAD+, *Lactobacillus*, and *Bifidobacterium*.

Figure 12:
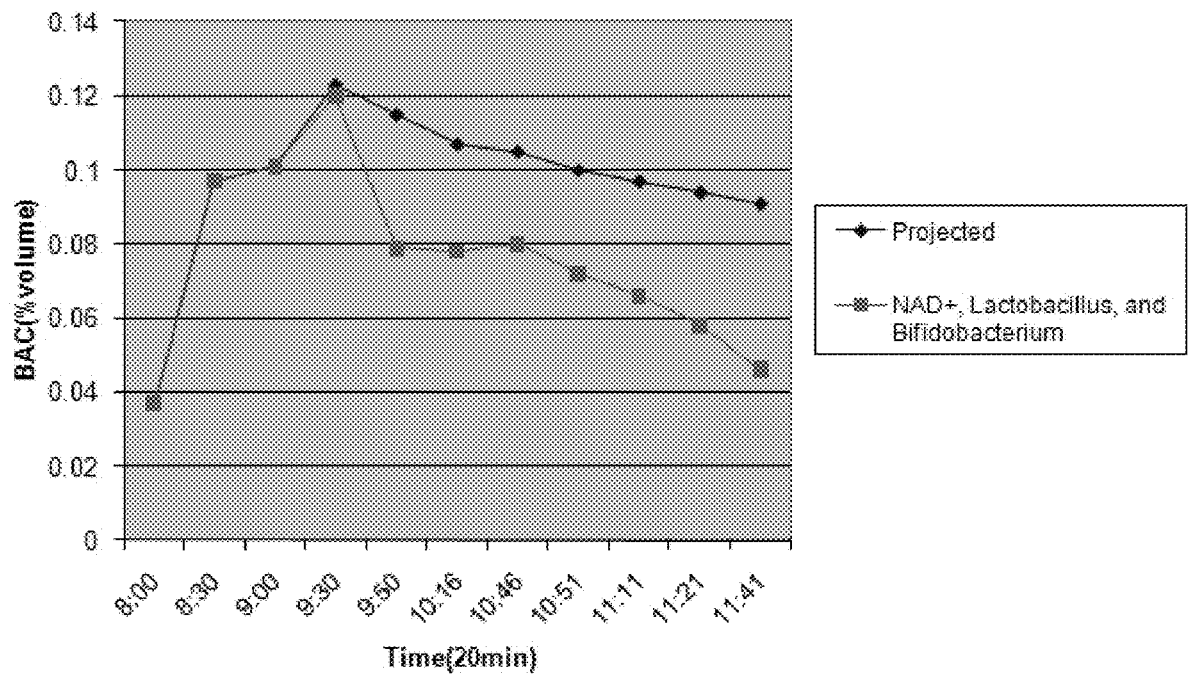
FIG. 12. A graph showing projected and actual BAC scores for a subject before and after administration of a composition comprising NAD+, *Lactobacillus*, and *Bifidobacterium*. The composition was administered at the time point labeled 9:50.

In the experiment shown in FIG. 12, a male subject age 64 weighing 185 pounds consumed wine. A composition comprising NAD+, *Lactobacillus*, and *Bifidobacterium* was administered at the time point labeled 9:50. At that time point, the subject's BAC was 0.12, and the subject exhibited signs of intoxication, including blurred vision, slurred speech, and loss of motor skills. At the 10:16 time point, the subject's projected BAC was 0.115, but the subject's actual BAC was only 0.079. At that time point, the subject's intoxication symptoms improved in that the subject's speech and motor skills improved. As shown in FIG. 12, the subject's actual BAC was greatly reduced as compared to the subject's projected BAC following administration of NAD+, *Lactobacillus*, and *Bifidobacterium*. Between the 9:50 and 10:16 time points, the subject's actual BAC was reduced by 34% with administration of NAD+, *Lactobacillus*, and *Bifidobacterium*, while the BAC was projected to decrease by only 6.5% without administration of NAD+, *Lactobacillus*, and *Bifidobacterium*.

Figure 13:
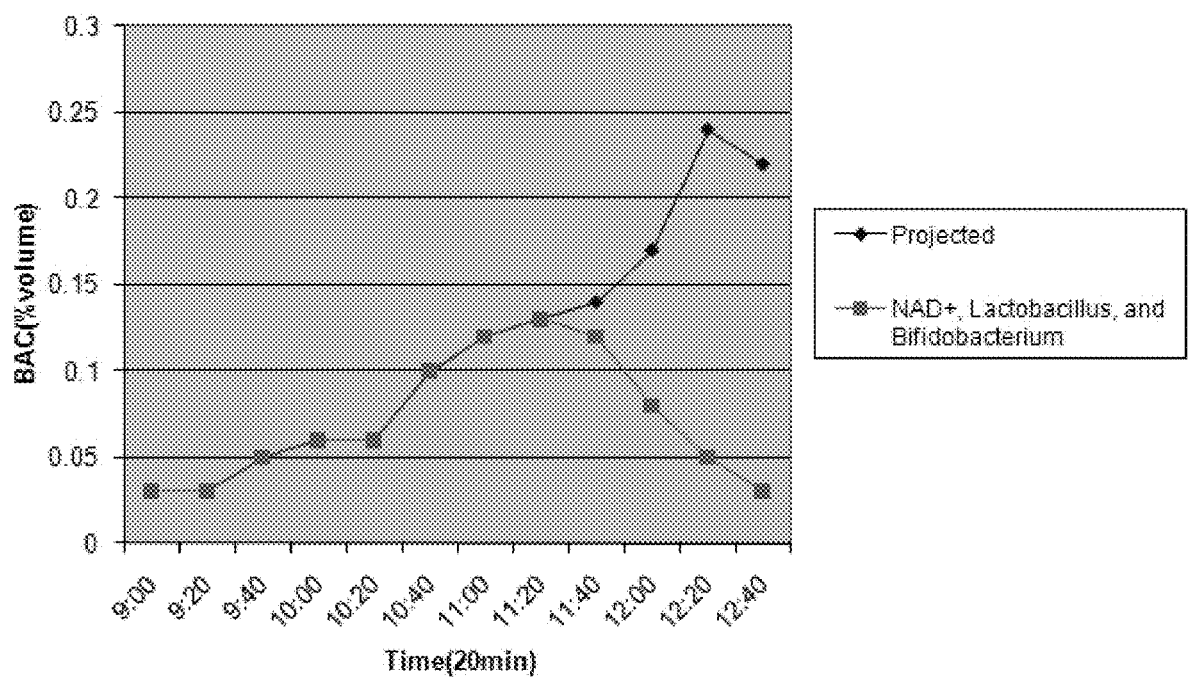
FIG. 13. A graph showing projected and actual BAC scores for a subject under binge-drinking conditions before and after administration of a composition comprising NAD+, *Lactobacillus*, and *Bifidobacterium*. The composition was administered at the time point labeled 11:20.

In the experiment shown in FIG. 13, a female subject age 23 weighing 130 pounds consumed vodka under binge-drinking conditions (meaning that the subject consumed the alcohol quickly). A composition comprising NAD+, *Lactobacillus*, and *Bifidobacterium* was administered at the time point labeled 11:20. At that time point, the subject's BAC was 0.13, and the subject exhibited signs of intoxication including loud speech and loss of motor skills. At the 12:00 time point (40 minutes after administration of the NAD+, *Lactobacillus*, and *Bifidobacterium*), the subject's projected BAC was 0.17, but the subject's actual BAC was only 0.08. Twenty minutes later, at the 12:20 time point, the subject's projected BAC was 0.24, but the subject's actual BAC was only 0.05, and the subjected no longer exhibited signs of intoxication. As shown in FIG. 13, the subject's actual BAC was greatly reduced as compared to the subject's projected BAC following administration of NAD+, *Lactobacillus*, and *Bifidobacterium*. Between the 11:20 and 12:20 time points, the subject's BAC was reduced by 62%. During that same 60 minute time period, it is projected that the subject's BAC would not have decreased absent administration of NAD+, *Lactobacillus*, and *Bifidobacterium*.

Figure 14:
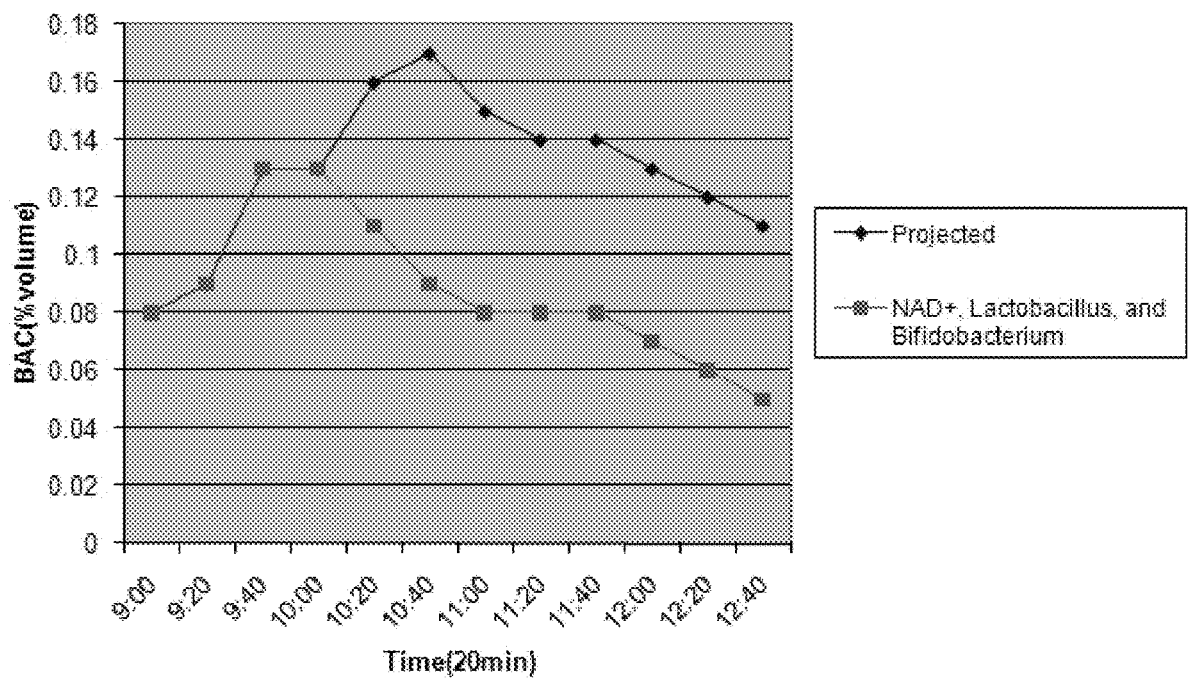
FIG. 14. A graph showing projected and actual BAC scores for a subject under binge-drinking conditions before and after administration of a composition comprising NAD+, *Lactobacillus*, and *Bifidobacterium*. The composition was administered at the time point labeled 10:00.

In the experiment shown in FIG. 14, a male subject age 26 weighing 170 pounds consumed vodka under binge-drinking conditions (meaning that the subject consumed the alcohol quickly). A composition comprising NAD+, *Lactobacillus*, and *Bifidobacterium* was administered at the time point labeled 10:00. At that time point, the subject's BAC was 0.13. Twenty minutes later, at the 10:20 time point, the subject's projected BAC was 0.16, while the subject's actual BAC was only 0.11. At the 11:00 time point, the subject's projected BAC was 0.15, while the subject's actual BAC was only 0.08. Thus, in the 60 minutes between the 10:00 and 11:00 time points, the subject experienced a 38% reduction in BAC. Without the NAD+, *Lactobacillus*, and *Bifidobacterium*, it is projected that the subject's BAC would not have decreased during that 60 minute time period.

Example 2

Additional probiotics, other than *Lactobacillus* and *Bifidobacterium*, can be used in the disclosed methods and compositions. Such probiotics may be tested as provided in Example 1.

Without wishing to be bound by theory, the inventors hypothesize that the synergistic results achieved by the disclosed methods and compositions result from an increase in First Pass Metabolism (FPM) of alcohol; elimination of alcohol vapors in the aerodigestive tract, intranasal systemic pathway, or intranasal brain pathway; and/or improved elimination of acetaldehyde. It is believed that the mechanism of action involves the activity of alcohol dehydrogenase enzymes (e.g., one or more of ADH1-7). Thus, probiotics that can survive and function in the human digestive tract (e.g., anaerobic probiotics); function in FPM; function in the aerodigestive tract, intranasal systemic pathway, or intranasal brain pathway; and/or provide significant alcohol dehydrogenase activity (such as provided by one or more of ADH1-7) are expected to be useful in the disclosed methods and compositions. Suitability of such probiotics in the inventive methods and compositions can be assessed as described in Example 1. Particular probiotics that may be useful in the disclosed methods and compositions include *Leuconostoc* (including *L. mesenteroides*, *L. citrovorum*), *Pediococcus*, Anaerobic *Streptococci*, *Peptococcus*, *Peptostreptococcus*, *Ruminococcus*, *Coprococcus*, *Sarcina*, *Bacillaceae* (including *B. Subtilis* and *B. cereus*), *Clostridium* (including *C. perfrigens*, *C. butyricum*, and *C. botulinum*), *Propionibacteriacea* (including *P. acnes*), *Eubacterium* (including *E. aerofaciens* and *E. rectal*), and *Saccharomyces* (including *S. boulardii*).

Similarly, recombinant or isolated enzymes, such as ADH enzymes, may be tested for suitability for use in rapidly reducing BAC using the test protocol described in Example 1. Any enzyme (e.g., ADH1-7) may be tested as described in Example 1. Particular ADH enzymes that may be useful include enzymes that function in FPM or function in the aerodigestive tract, intranasal systemic pathway, or intranasal brain pathway. For example, ADH-7 and other members of the ADH IV family may be useful in methods and compositions for rapidly reducing BAC.

The invention claimed is:

1. A composition comprising 25-100 billion cfu of *Lactobacillus*, 25-100 billion cfu of *Bifidobacterium*, 5-15 mg of NAD+, vitamin E, and a vitamin B.

2. The composition of claim 1, wherein the composition further comprises zinc and Coenzyme Q10.

3. The composition of claim 1, wherein the *Lactobacillus* comprises *Lactobacillus* GG, *L. acidophilus* DDS-1, *L. casei*, *L. plantarum*, *L. salivarius*, *L. rhamnosus*, or *L. brevis*.

4. A method of reducing blood alcohol content in a subject having an elevated blood alcohol content, the method comprising administering the composition of claim 1 to the subject, wherein the subject's blood alcohol content is reduced by said administration.

5. The method of claim 4, wherein the *Bifidobacterium* comprises *B. lactis*, *B. longum*, *B. infantis*, or *B. bifidum*.

6. The method of claim 4, further comprising providing zinc to the subject.

7. The method of claim 4, further comprising providing an antioxidant to the subject.

8. The method of claim 7, wherein the antioxidant is Coenzyme Q10.

* * * * *